US008058467B2

(12) United States Patent
Ongini et al.

(10) Patent No.: US 8,058,467 B2
(45) Date of Patent: *Nov. 15, 2011

(54) PROSTAGLANDIN DERIVATIVES

(75) Inventors: Ennio Ongini, Milan (IT); Valerio Chiroli, Milan (IT); Francesca Benedini, Milan (IT); Piero Del Soldato, Monza (IT)

(73) Assignee: Nicox S.A., Sophia Antipolis-Valbonne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/025,740

(22) Filed: Feb. 11, 2011

(65) Prior Publication Data

US 2011/0136904 A1 Jun. 9, 2011

Related U.S. Application Data

(63) Continuation of application No. 12/613,985, filed on Nov. 6, 2009, now Pat. No. 7,910,767, which is a continuation of application No. 12/210,975, filed on Sep. 15, 2008, now Pat. No. 7,629,345, which is a continuation of application No. 11/841,628, filed on Aug. 20, 2007, now Pat. No. 7,449,469, which is a continuation of application No. 11/029,698, filed on Jan. 5, 2005, now Pat. No. 7,273,946.

(30) Foreign Application Priority Data

Jan. 5, 2004 (EP) .................................... 04100001

(51) Int. Cl.
C07C 69/76 (2006.01)
A61K 31/44 (2006.01)
A61K 31/49 (2006.01)

(52) U.S. Cl. ...................................... 560/8; 514/255.01

(58) Field of Classification Search .. 560/8; 514/255.01
See application file for complete search history.

(56) References Cited

U.S. PATENT DOCUMENTS

| 3,922,293 | A | 11/1975 | Morozowich |
| 4,952,581 | A | 8/1990 | Bito et al. |
| 5,625,083 | A | 4/1997 | Bezuglov et al. |
| 5,811,443 | A | 9/1998 | DeSantis, Jr. et al. |
| 6,211,233 | B1 | 4/2001 | Del Soldato |
| 6,242,432 | B1 | 6/2001 | Del Soldato |
| 6,417,228 | B1 | 7/2002 | Klimko |
| 7,273,946 | B2 | 9/2007 | Ongini et al. |
| 7,449,469 | B2 | 11/2008 | Ongini et al. |
| 7,629,345 | B2 | 12/2009 | Ongini et al. |

FOREIGN PATENT DOCUMENTS

| EP | 04100001.9 | 1/2004 |
| WO | WO 90/02553 A1 | 3/1990 |
| WO | WO 94/10141 A1 | 5/1994 |
| WO | WO 98/58910 A1 | 12/1998 |
| WO | WO 00/51978 A1 | 9/2000 |
| WO | WO 2005/068421 A1 | 7/2005 |

OTHER PUBLICATIONS

Alm, A., "Prostaglandin Derivatives As Ocular Hypotensive Agents," *Progress in Retinal and Eye Research*, 1997, 291-312, vol. 17, No. 3.
Arnaud, C.H., "Drug Hybrids Enter the Fray" *Chemical & Engineering News*, 2007, 46-48, vol. 85, No. 46.
Beers, M.H., et al., The Merck Manual of Diagnosis and Therapy, Section 8, Chapter 100; 1995-2001.
Greene, T.W., "Protective Groups in Organic Synthesis," Harvard University Press, 1980, 14-118.
Greene, T.W., "Protective Groups in Organic Synthesis," Harvard University Press, 1980, 68-86.

*Primary Examiner* — Sikarl Witherspoon
(74) *Attorney, Agent, or Firm* — Arent Fox LLP

(57) ABSTRACT

Prostaglandin nitroderivatives having improved pharmacological activity and enhanced tolerability are described. They can be employed for the treatment of glaucoma and ocular hypertension.

2 Claims, No Drawings

PROSTAGLANDIN DERIVATIVES

CROSS-REFERENCE TO RELATED APPLICATION

This is a Continuation application, which claims benefit of U.S. patent application Ser. No. 12/613,985 filed Nov. 6, 2009, which is a continuation of U.S. patent application Ser. No. 12/210,975 filed Sep. 15, 2008, now patented U.S. Pat. No. 7,629,345, which is a continuation of U.S. patent application Ser. No. 11/841,628 filed Aug. 20, 2007, now patented U.S. Pat. No. 7,449,469, which is a continuation of U.S. patent application Ser. No. 11/029,698 filed Jan. 5, 2005, now patented U.S. Pat. No. 7,273,946, which claims priority from European Patent Application No. 04100001.9 filed Jan. 5, 2004. The disclosures of these prior applications are hereby incorporated herein in their entirety by reference.

BACKGROUND OF THE INVENTION

The present invention relates to new prostaglandin derivatives. More particularly, the present invention relates to prostaglandin nitrooxyderivatives, pharmaceutical corn positions containing them and their use as drugs for treating glaucoma and ocular hypertension.

Glaucoma is optic nerve damage, often associated with increased intraocular pressure (IOP), that leads to progressive, irreversible loss of vision.

Almost 3 million people in the United States and 14 million people worldwide have glaucoma; this is the third leading cause of blindness worldwide.

Glaucoma occurs when an imbalance in production and drainage of fluid in the eye (aqueous humor) increases eye pressure to unhealthy levels.

It is known that elevated IOP can be at least partially controlled by administering drugs which either reduce the production of aqueous humor within the eye or increase the fluid drainage, such as beta-blockers, α-agonists, cholinergic agents, carbonic anhydrase inhibitors, or prostaglandin analogs.

Several side effects are associated with the drugs conventionally used to treat glaucoma.

Topical beta-blockers show serious pulmonary side effects, depression, fatigue, confusion, impotence, hair loss, heart failure and bradycardia.

Topical α-agonists have a fairly high incidence of allergic or toxic reactions; topical cholinergic agents (miotics) can cause visual side effects.

The side effects associated with oral carbonic anhydrase inhibitors include fatigue, anorexia, depression, paresthesias and serum electrolyte abnormalities (The Merck Manual of Diagnosis and Therapy, Seventeenth Edition, M. H. Beers and R. Berkow Editors, Sec. 8, Ch. 100).

Finally, the topical prostaglandin analogs (bimatoprost, latanoprost, travoprost and unoprostone) used in the treatment of glaucoma, can produce ocular side effects, such as increased pigmentation of the iris, ocular irritation, conjunctival hyperaemia, iritis, uveitis and macular oedema (Martindale, Thirty-third edition, p. 1445).

U.S. Pat. No. 3,922,293 describes monocarboxyacylates of prostaglandins F-type and their 15β isomers, at the C-9 position, and processes for preparing them; U.S. Pat. No. 6,417,228 discloses 13-aza prostaglandins having functional $PGF_{2\alpha}$ receptor agonist activity and their use in treating glaucoma and ocular hypertension.

WO 90/02553 discloses the use of prostaglandins derivatives of PGA, PGB, PGE and PGF, in which the omega chain contains a ring structure, for the treatment of glaucoma or ocular hypertension.

WO 00/51978 describes novel nitrosated and/or nitrosylated prostaglandins, in particular novel derivatives of $PGE_1$, novel compositions and their use for treating sexual dysfunctions.

U.S. Pat. No. 5,625,083 discloses dinitroglycerol esters of prostaglandins which may be used as vasodilators, antihypertensive cardiovascular agents or bronchodilators.

U.S. Pat. No. 6,211,233 discloses compounds of the general formula $A\text{-}X_1\text{—}NO_2$, wherein A contains a prostaglandin residue, in particular $PGE_1$, and $X_1$ is a bivalent connecting bridge, and their use for treating impotence.

SUMMARY OF THE INVENTION

It is an object of the present invention to provide new derivatives of prostaglandins able not only to eliminate or at least reduce the side effects associated with these compounds, but also to possess an improved pharmacological activity. It has been surprisingly found that prostaglandin nitroderivatives have a significantly improved overall profile as compared to native prostaglandins both in terms of wider pharmacological activity and enhanced tolerability. In particular, it has been recognized that the prostaglandin nitroderivatives of the present invention can be employed for treating glaucoma and ocular hypertension. The compounds of the present invention are indicated for the reduction of intraocular pressure in patients with open-angle glaucoma or with chronic angle-closure glaucoma who underwent peripheral iridotomy or laser iridoplasty.

DETAILED DESCRIPTION OF THE INVENTION

An object of the present invention is, therefore, prostaglandin nitroderivatives of general formula (I) and pharmaceutically acceptable salts or stereoisomers thereof.

R—X—Y—ONO₂    (I)

wherein R is the prostaglandin residue of formula (II):

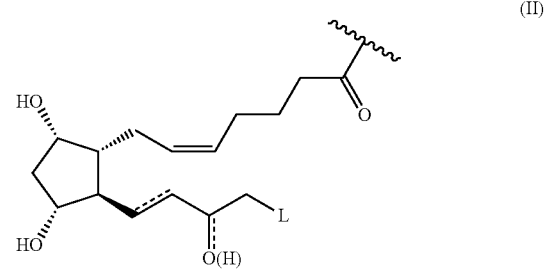

wherein
the symbol ⚌ represents a single bond or a double bond;
L is selected from the following groups:

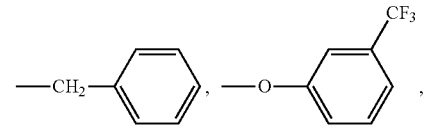

-continued

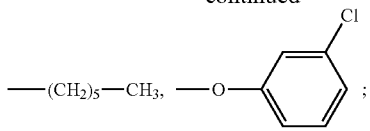

X is —O—, or —S— or —NH—;
Y is a bivalent radical having the following meaning:

a)
straight or branched $C_1$-$C_{20}$ alkylene, preferably $C_1$-$C_{10}$, being optionally substituted with one or more of the substituents selected from the group consisting of: halogen atoms, hydroxy, —$ONO_2$ or T, wherein T is —OC(O)($C_1$-$C_{10}$ alkyl)-$ONO_2$ or —O($C_1$-$C_{10}$ alkyl)-$ONO_2$;

cycloalkylene with 5 to 7 carbon atoms into cycloalkylene ring, the ring being optionally substituted with side chains $T_1$, wherein $T_1$ is straight or branched $C_1$-$C_{10}$ alkyl, preferably $CH_3$;

b)
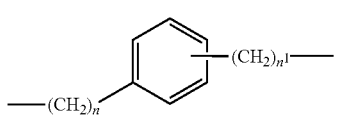

c)
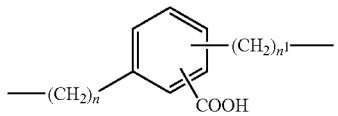

wherein n is an integer from 0 to 20, and $n^1$ is an integer from 1 to 20;

d)
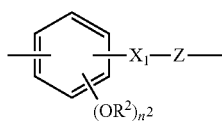

wherein
$X_1$=—OCO— or —COO— and $R^2$ is H or $CH_3$;
Z is —$(CH)_{n^1}$— or the bivalent radical defined above under b)
$n^1$ is as defined above and $n^2$ is an integer from 0 to 2;

e)
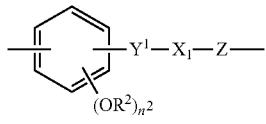

wherein;
$Y^1$ is —$CH_2$—$CH_2$—$(CH_2)_{n^2}$—; or —CH=CH—$(CH_2)_{n^2}$—;
Z is —$(CH)_{n^1}$— or the bivalent radical defined above under b)
$n^1$, $n^2$, $R^2$ and $X_1$ are as defined above;

f)
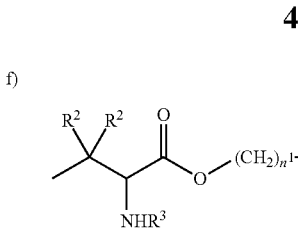

wherein:
$n^1$ and $R^2$ are as defined above, $R^3$ is H or —$COCH_3$;
with the proviso that when Y is selected from the bivalent radicals mentioned under b)-f), the terminal —$ONO_2$ group is bound to —$(CH_2)_{n^1}$;

g)
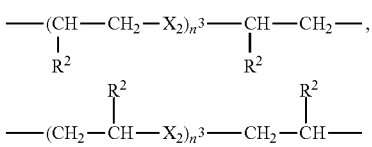

wherein $X_2$ is —O— or —S—, $n^3$ is an integer from 1 to 6, preferably from 1 to 4, $R^2$ is as defined above;

h)
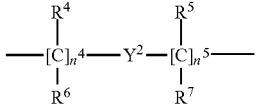

wherein:
$n^4$ is an integer from 0 to 10;
$n^5$ is an integer from 1 to 10;
$R^4$, $R^5$, $R^6$, $R^7$ are the same or different, and are H or straight or branched $C_1$-$C_4$ alkyl, preferably $R^4$, $R^5$, $R^6$, $R^7$ are H;
wherein the —$ONO_2$ group is linked to

wherein $n^5$ is as defined above;
$Y^2$ is an heterocyclic saturated, unsaturated or aromatic 5 or 6 members ring, containing one or more heteroatoms selected from nitrogen, oxygen, sulfur,
and is selected from

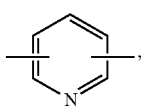   (Y1)

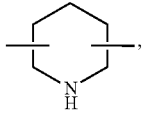   (Y2)

(Y3) 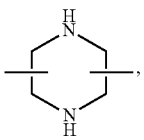

(Y4) 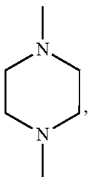

(Y5) 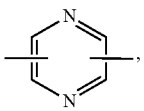

(Y6) 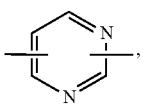

(Y7) 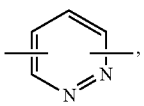

(Y8) 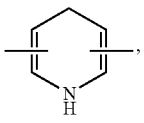

(Y9) 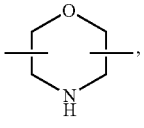

(Y10) 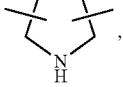

(Y11) 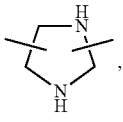

(Y12) 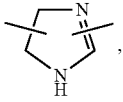

(Y13) 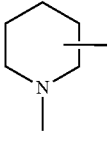

The term "$C_1$-$C_{20}$ alkylene" as used herein refers to branched or straight chain $C_1$-$C_{20}$ hydrocarbon, preferably having from 1 to 10 carbon atoms such as methylene, ethylene, propylene, isopropylene, n-butylene, pentylene, n-hexylene and the like.

The term "$C_1$-$C_{10}$ alkyl" as used herein refers to branched or straight chain alkyl groups comprising one to ten carbon atoms, including methyl, ethyl, n-propyl, isopropyl, n-butyl, isobutyl, t-butyl, pentyl, hexyl, octyl and the like.

The term "cycloalkylene" as used herein refers to ring having from 5 to 7 carbon atoms including, but not limited to, cyclopentylene, cyclohexylene optionally substituted with side chains such as straight or branched ($C_1$-$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminum hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures.

Within the scope of the invention are also all the possible isomers, stereoisomers and their mixtures of the compounds of formula (I), including mixtures enriched in a particular isomer.

Preferred compounds of formula (I) are those wherein R, L, X are as defined in claim 1 and Y is a bivalent radical having the following meaning:

a)
straight or branched $C_1$-$C_{20}$ alkylene, being optionally substituted with one or more of the substituents selected from the group consisting of: halogen atoms, hydroxy, —$ONO_2$ or T, wherein T is
—$OC(O)(C_1$-$C_{10}$ alkyl)-$ONO_2$ or —$O(C_1$-$C_{10}$ alkyl)-$ONO_2$;

cycloalkylene with 5 to 7 carbon atoms into cycloalkylene ring, the ring being optionally substituted with side chains $T_1$, wherein $T_1$ is straight or branched $C_1$-$C_{10}$ alkyl;

b)
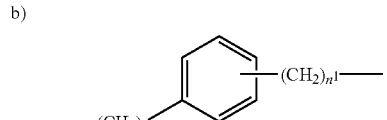

c)
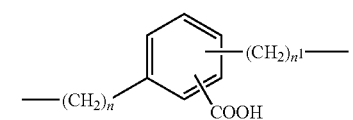

wherein n is an integer from 0 to 20, and $n^1$ is an integer from 1 to 20;

d)
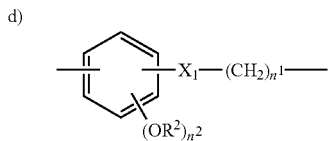

wherein:
$n^1$ is as defined above and $n^2$ is an integer from 0 to 2;
$X_1$=—OCO— or —COO— and $R^2$ is H or $CH_3$;

e)
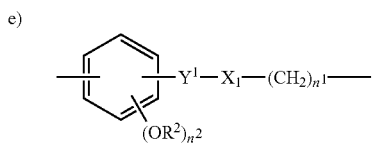

wherein:
$n^1$, $n^2$, $R^2$ and $X_1$ are as defined above;
$Y^1$ is —$CH_2$—$CH_2$— or —CH=CH—$(CH_2)_{n^2}$—;

f)
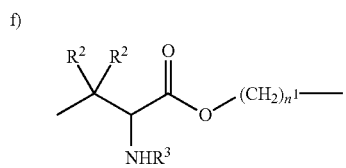

wherein:
$n^1$ and $R^2$ are as defined above, $R^3$ is H or —$COCH_3$;
with the proviso that when Y is selected from the bivalent radicals mentioned under b)-f), the —$ONO_2$ group is bound to —$(CH_2)_{n^1}$;

g)
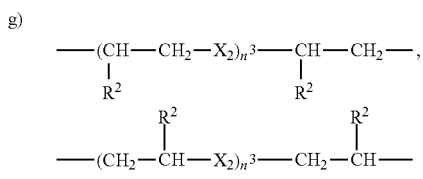

wherein $X_2$ is —O— or —S—, $n^3$ is an integer from 1 to 6 and $R^2$ is as defined above;

h)
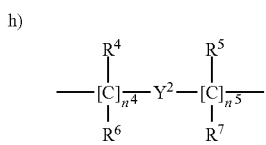

wherein:
$n^4$ is an integer from 0 to 10;
$n^5$ is an integer from 1 to 10;
$R^4$, $R^5$, $R^6$, $R^7$ are the same or different, and are H or straight or branched $C_1$-$C_4$ alkyl;

wherein the —$ONO_2$ group is linked to

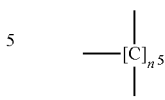

wherein $n^5$ is as defined above;
$Y^2$ is an heterocyclic saturated, unsaturated or aromatic 5 or 6 members ring, containing one or more heteroatoms selected from nitrogen, oxygen, sulfur,
and is selected from

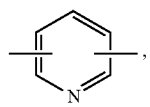 (Y1)

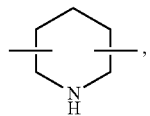 (Y2)

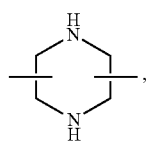 (Y3)

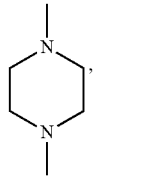 (Y4)

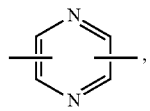 (Y5)

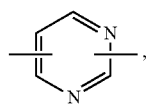 (Y6)

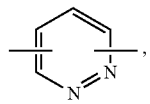 (Y7)

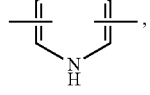 (Y8)

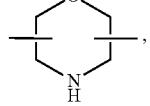 (Y9)

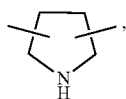 (Y10)

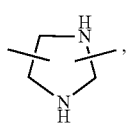 (Y11)

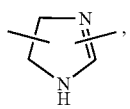 (Y12)

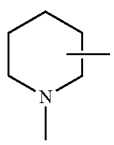 (Y13)

Preferred compounds of formula (I) are those wherein the prostaglandin residue R is selected from the group consisting of latanoprost, travoprost, unoprostone and cloprostenol, preferably R is latanoprost.

X is preferably —O— or —S—;

A preferred group of compounds of general formula (I) are those wherein Y is a bivalent radical having the following meaning:

a)
straight or branched $C_2$-$C_6$ alkylene, being optionally substituted with —$ONO_2$ or T, wherein T is as above defined;

b)
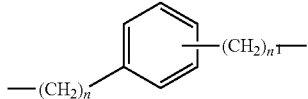

wherein n is an integer from 0 to 5, and $n^1$ is an integer from 1 to 5;

g)
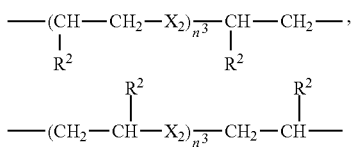

wherein $X_2$ is —O— or —S—, $n^3$ is 1, $R^2$ is as defined above.

Most preferred meanings of Y are:

a) branched $C_2$-$C_6$ alkylene or straight or branched $C_2$-$C_6$ alkylene being optionally substituted with —$ONO_2$ or T, wherein T is as defined in claim 1;

b)
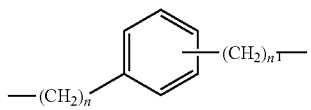

wherein n is 0, and $n^1$ is 1.

g)
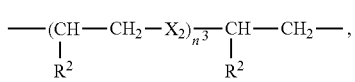

wherein $X_2$ is —O— or —S—, $n^3$ is 1, $R^2$ is hydrogen;

Another preferred group of compounds of general formula (I) are those wherein Y is a bivalent radical having the following meaning:

d)
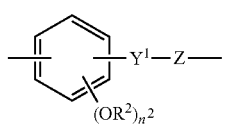

wherein $X_1$=—OCO— or —COO— and $R^2$ is H or $CH_3$;

Z is —$(CH)_n^1$— or the bivalent radical defined above under b) wherein n is an integer from 0 to 5;

$n^1$ is an integer from 1 to 5 and $n^2$ is an integer from 0 to 2;

e)
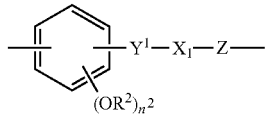

wherein:

$Y^1$ is —$CH_2$—$CH_2$—$(CH_2)_n^2$—; or —CH=CH—$(CH_2)_2$—;

Z is —$(CH)_n^1$— or the bivalent radical defined above under b)

$n^1$, $n^2$, $R^2$ and $X_1$ are as defined above;

f)
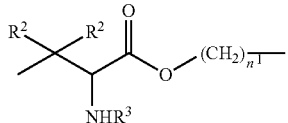

wherein:

$n^1$ and $R^2$ are as defined above, $R^3$ is H or $COCH_3$;

with the proviso that when Y is selected from the bivalent radicals mentioned under b)-f), the —$ONO_2$ group is bound to —$(CH_2)_n^1$;

h)

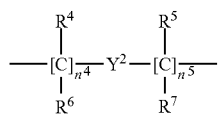

wherein:
$n^4$ is an integer from 0 to 3;
$n^5$ is an integer from 1 to 3;
$R^4$, $R^5$, $R^6$, $R^7$ are the same and are H;
and wherein the —$ONO_2$ group is linked to

$Y^2$ is a 6 member saturated, unsaturated or aromatic heterocyclic ring, containing one or two atoms of nitrogen and selected for example from

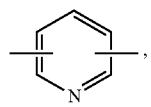
(Y1)

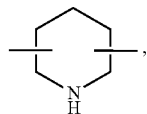
(Y2)

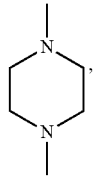
(Y4)

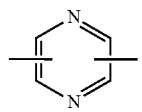
(Y5)

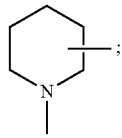
(Y13)

The following are preferred compounds according to the present invention:

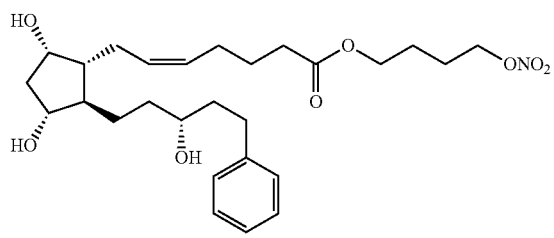
(1)

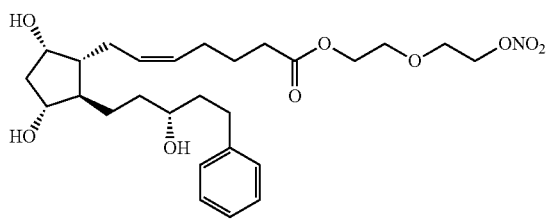
(2)

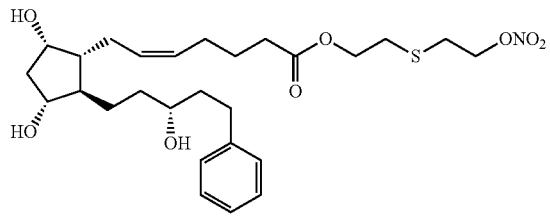
(3)

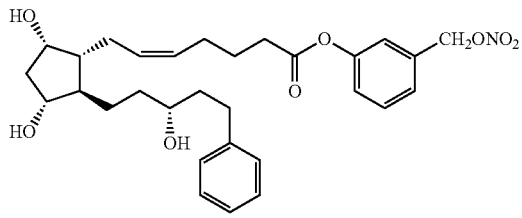
(4)

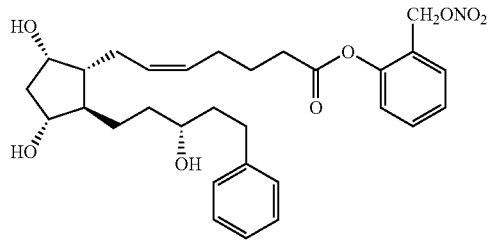
(5)

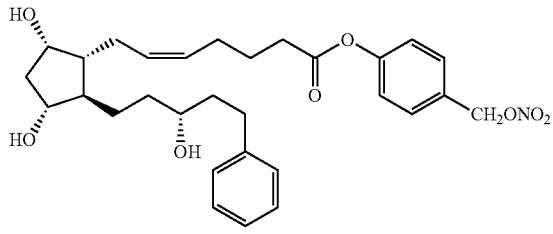
(6)

-continued
(7)
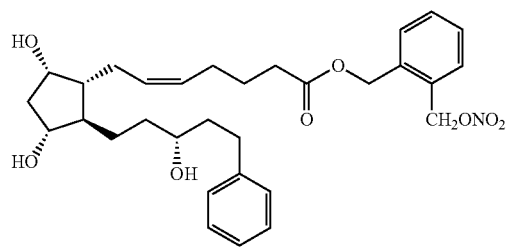
(8)
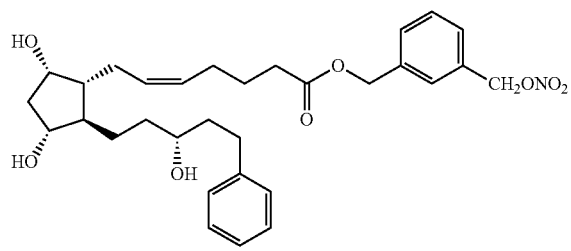
(9)
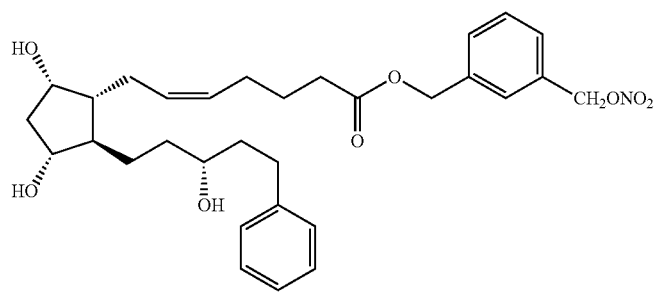
(10)
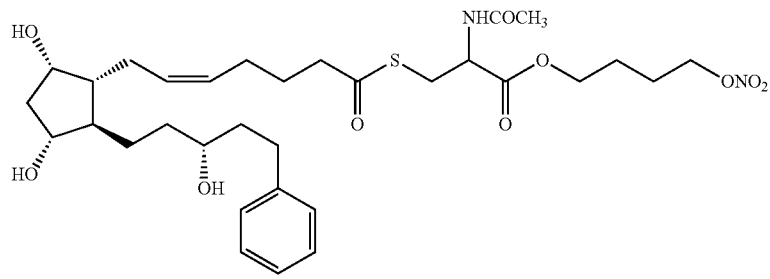
(11)
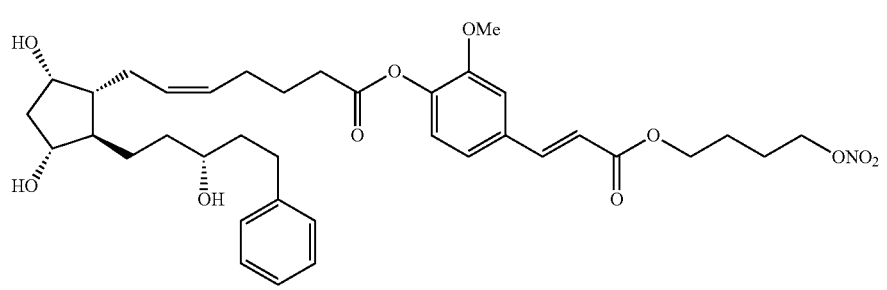
(12)
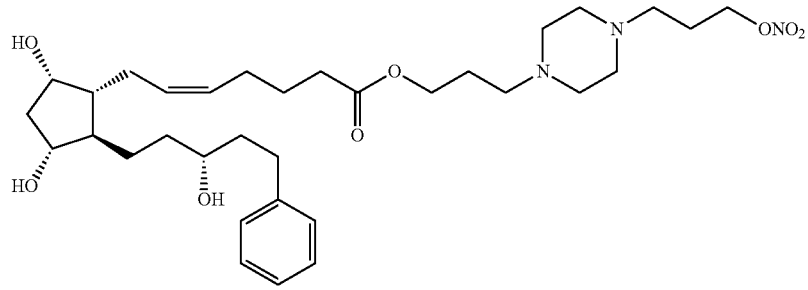

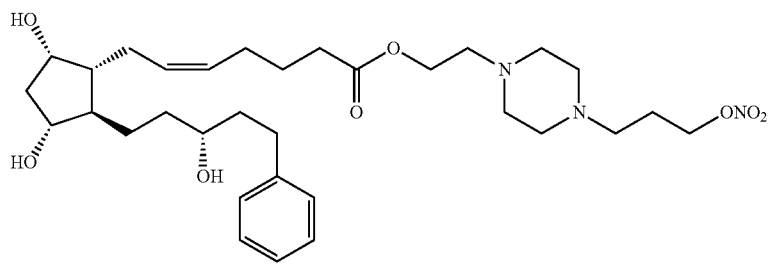
(13)
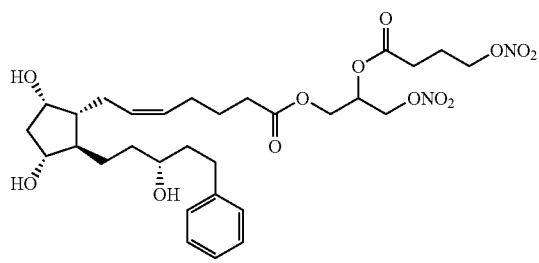
(14)
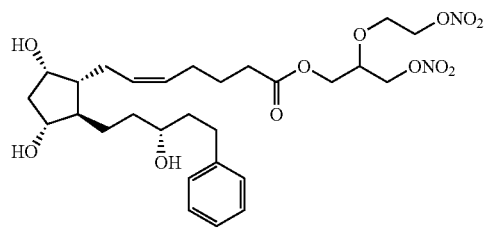
(15)
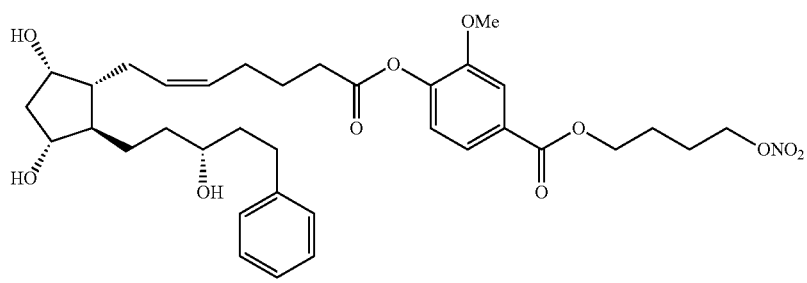
(16)
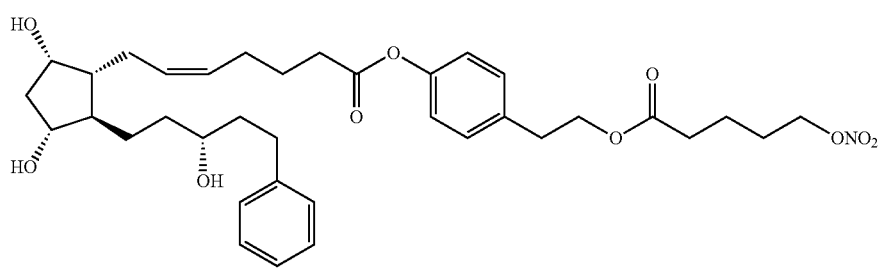
(18)
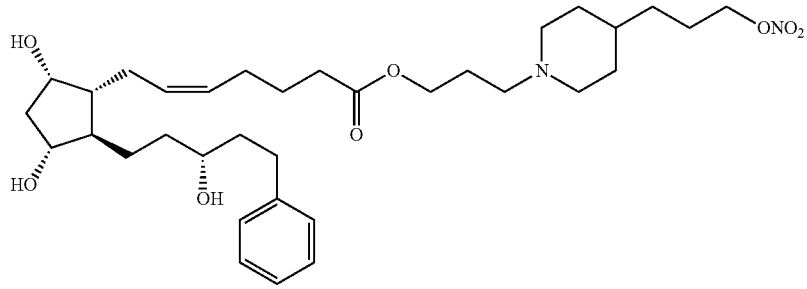
(19)

-continued
(20)
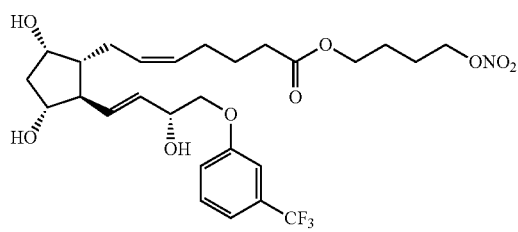
(21)
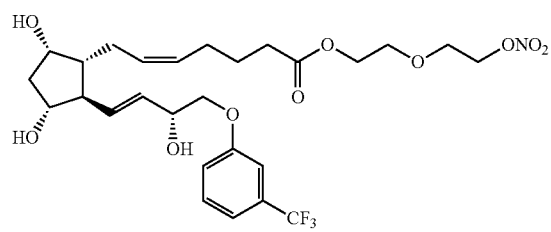
(22)
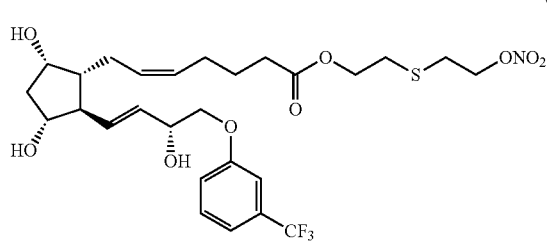
(23)
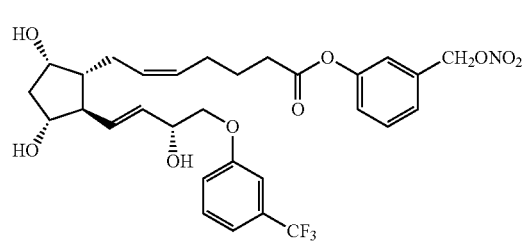
(24)
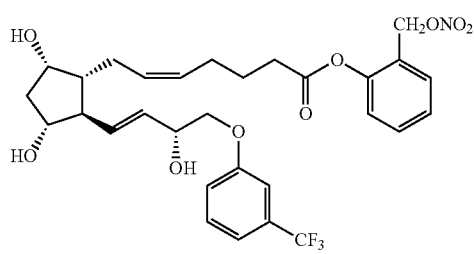
(25)
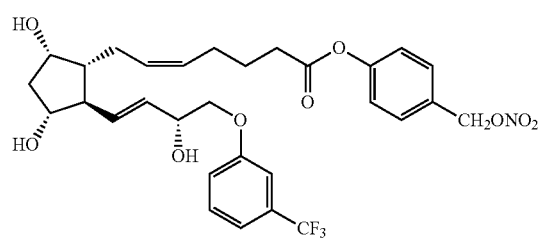
(26)
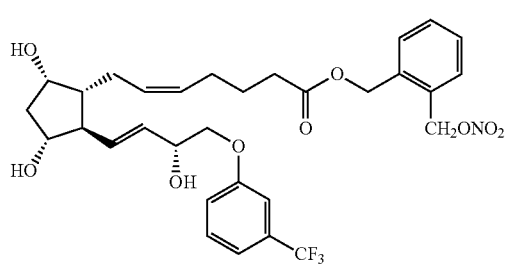
(27)
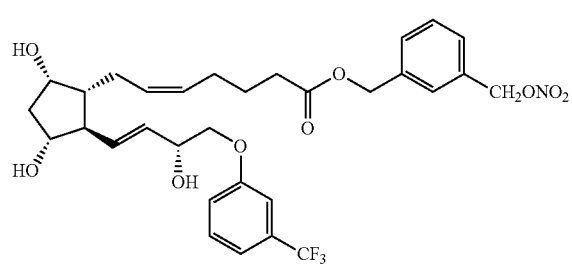
(28)
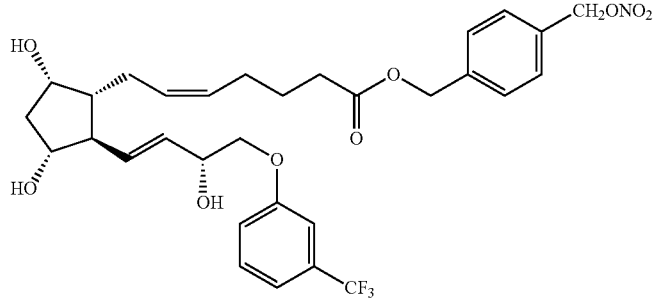

-continued
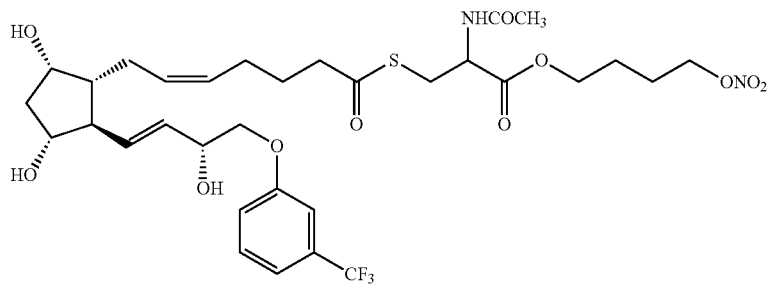
(29)
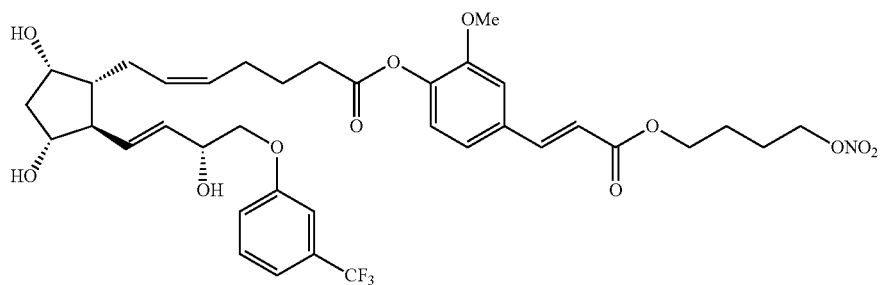
(30)
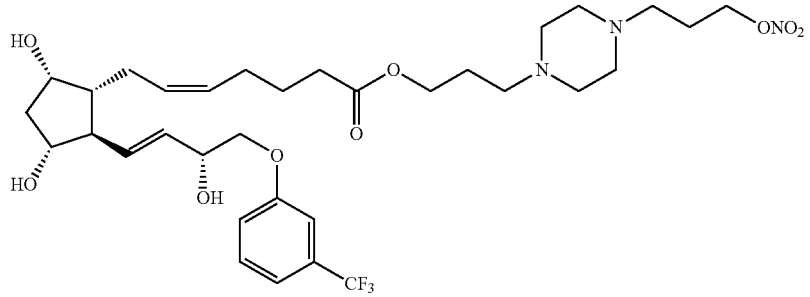
(31)
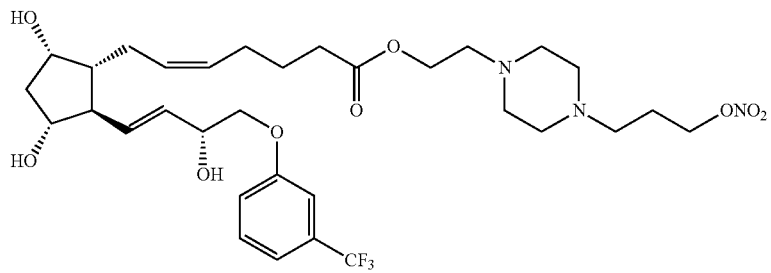
(32)
(33)
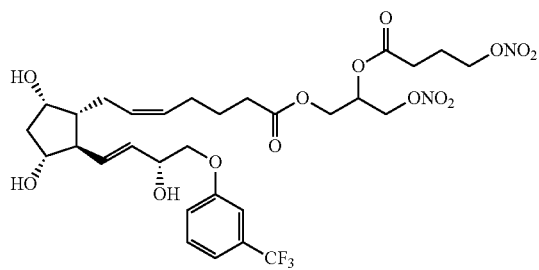
(34)
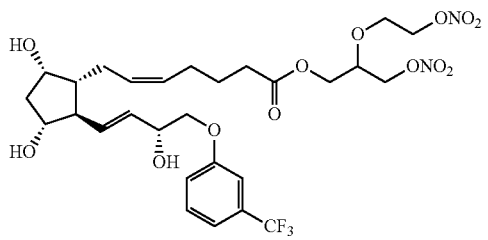

(35)
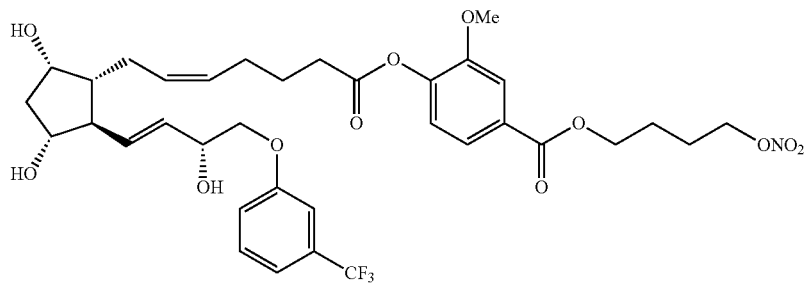
(37)
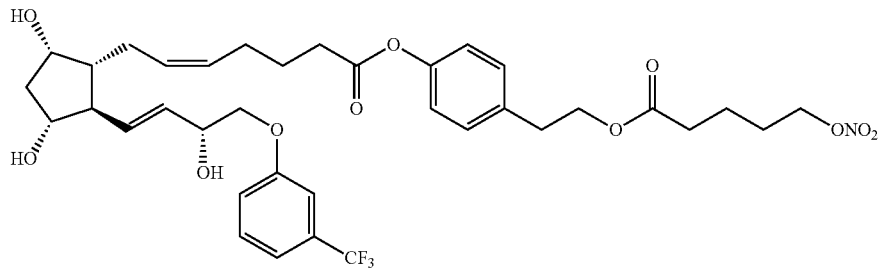
(38)
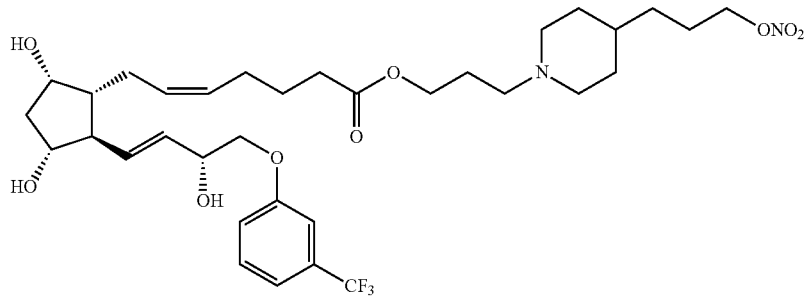
(39)
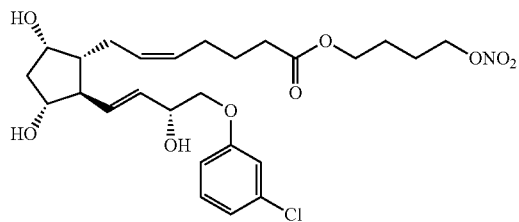
(40)
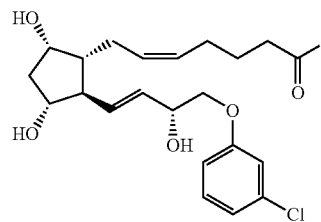
(41)
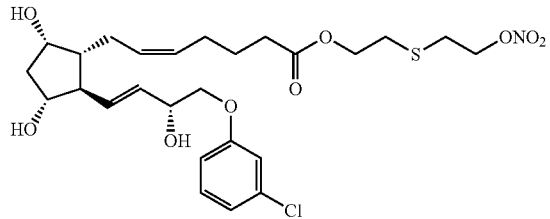
(42)
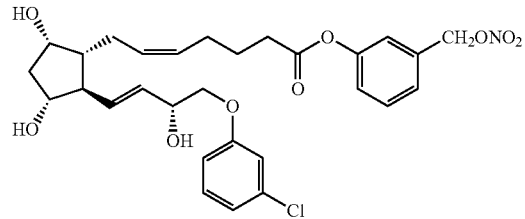

-continued
(43)
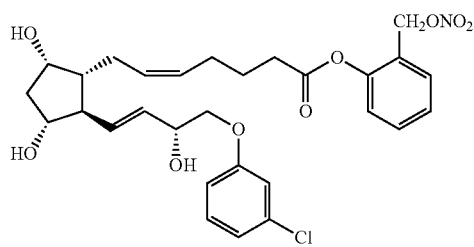
(44)
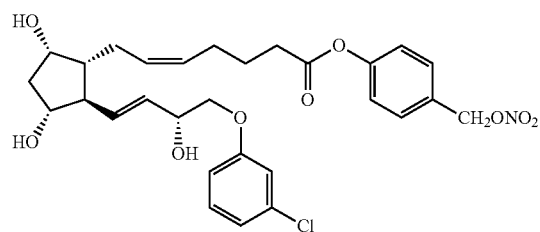
(45)
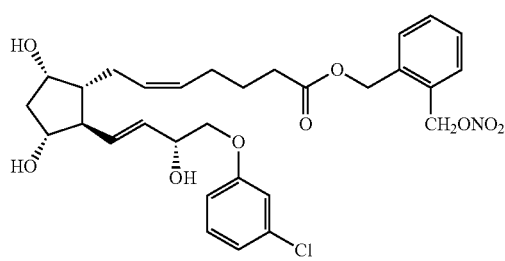
(46)
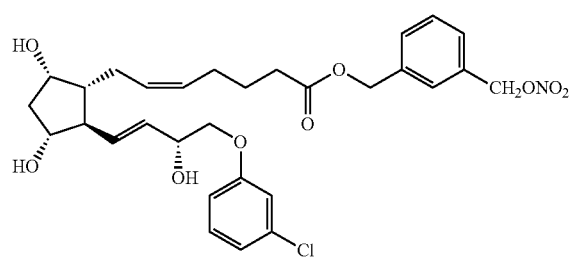
(47)
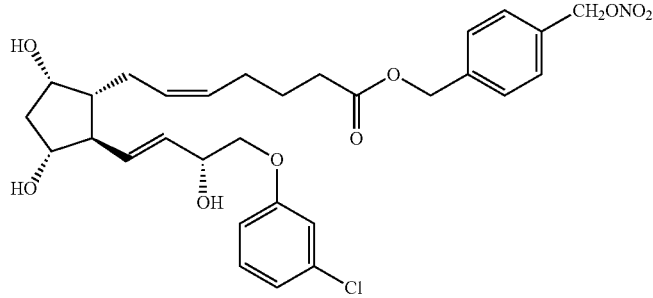
(48)
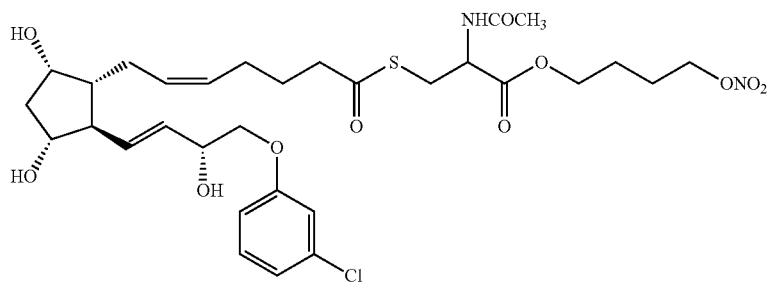
(49)
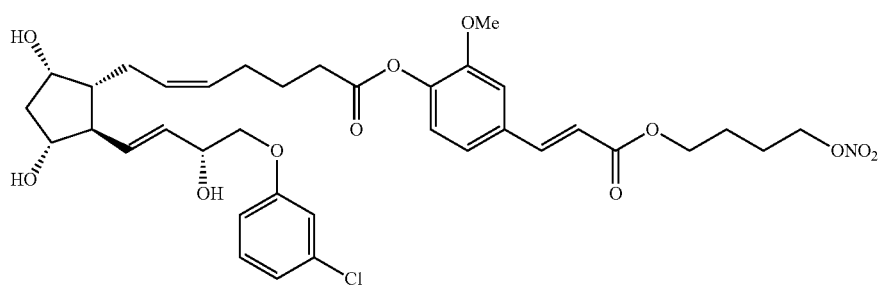

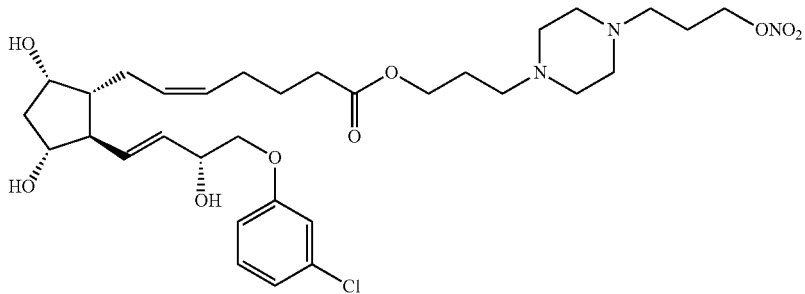
(50)
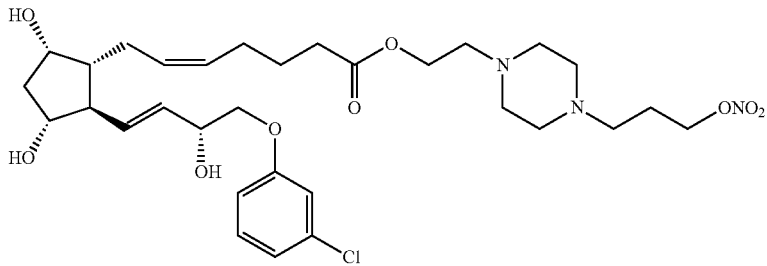
(51)
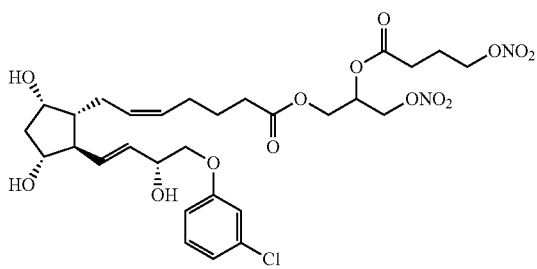
(52)
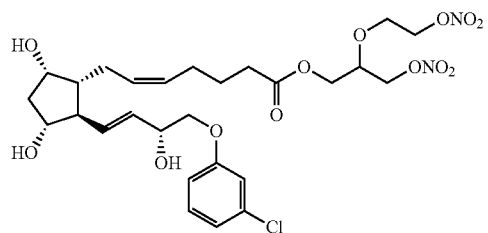
(53)
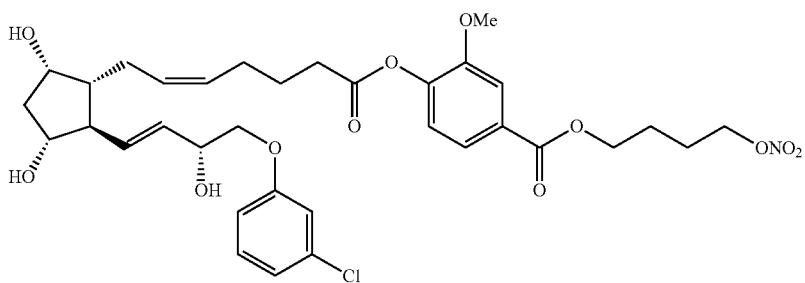
(54)
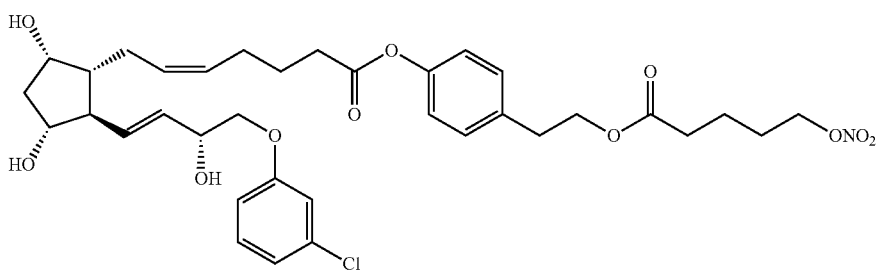
(56)

(57)
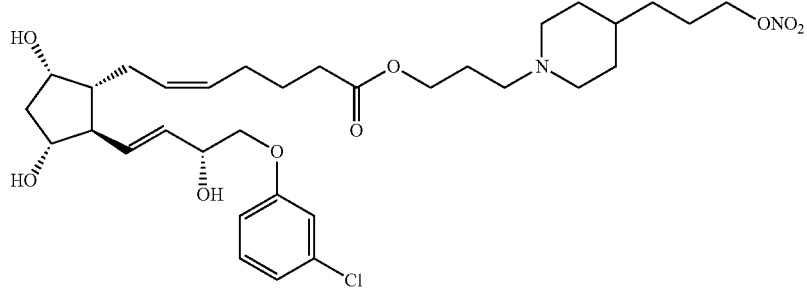
(58)
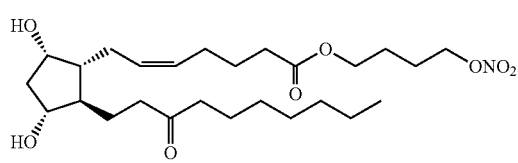
(59)
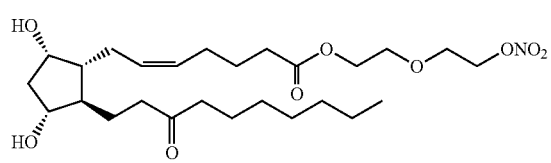
(60)
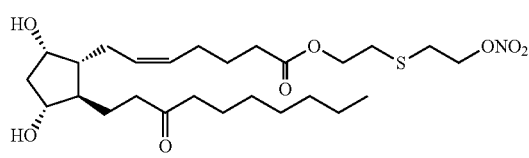
(61)
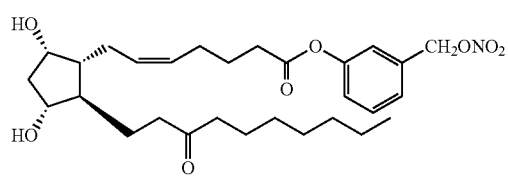
(62)
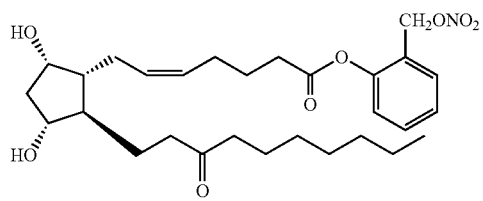
(63)
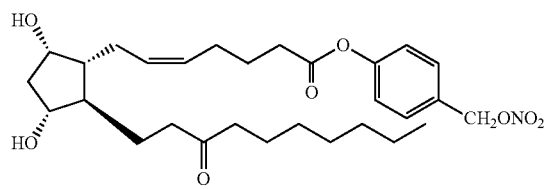
(64)
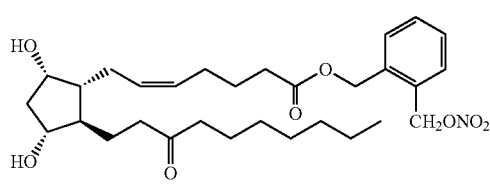
(65)
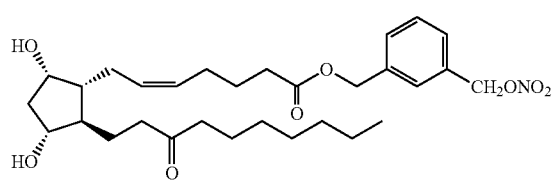
(66)
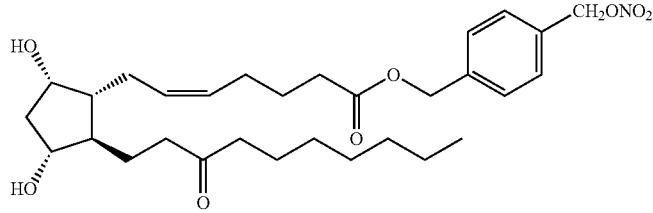

-continued
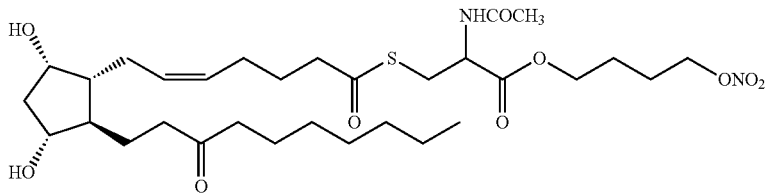
(67)
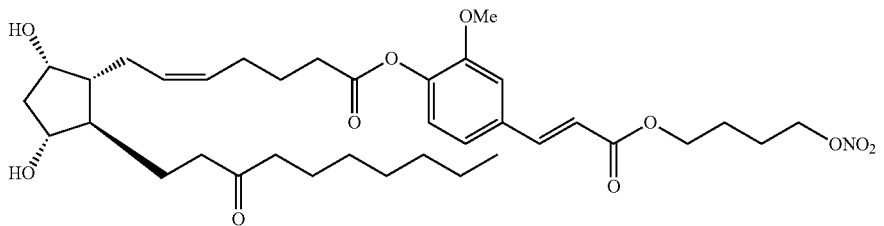
(68)
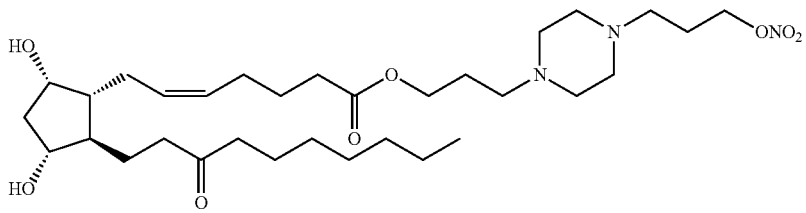
(69)
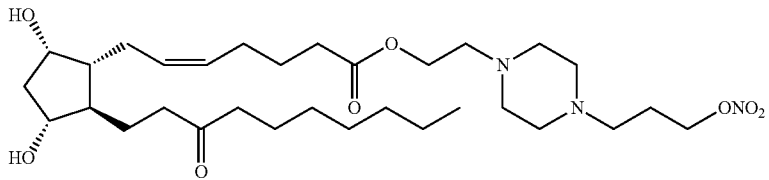
(70)
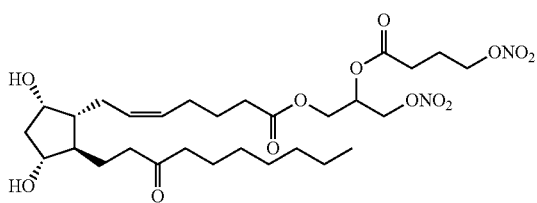
(71)
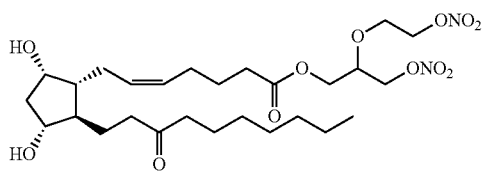
(72)
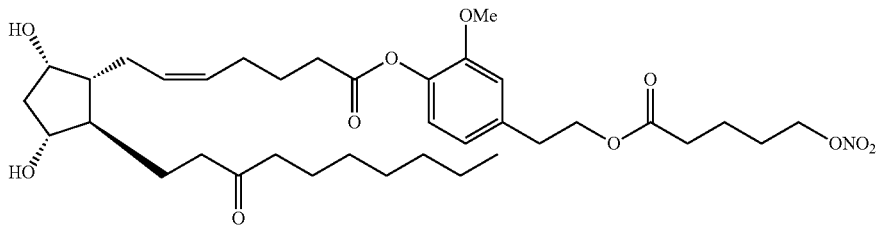
(73)
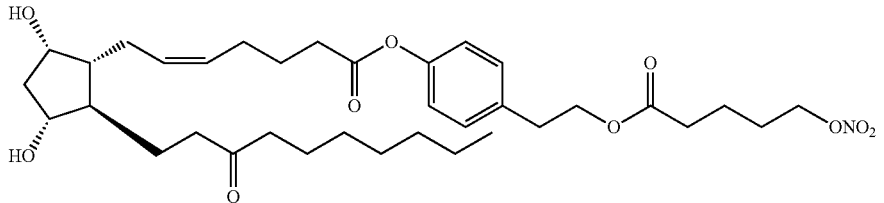
(75)

-continued
(76)
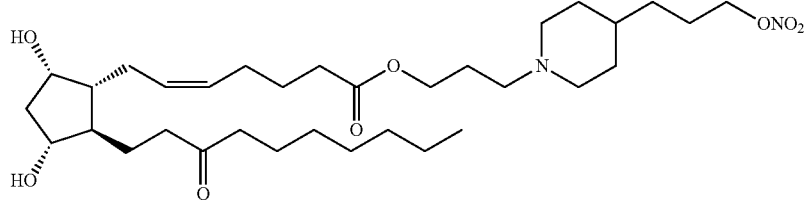
(77)
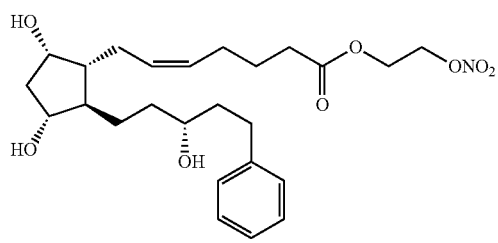
(78)
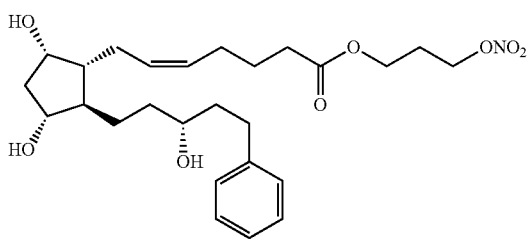
(79)
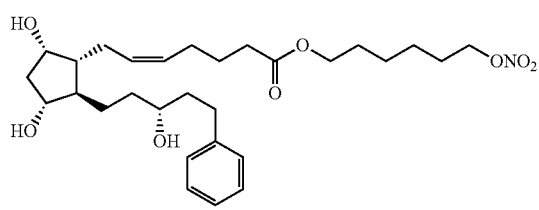
(80)
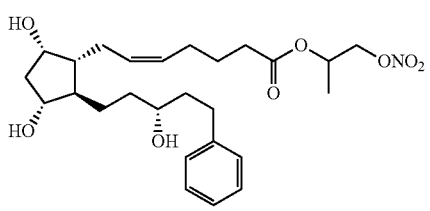
(81)
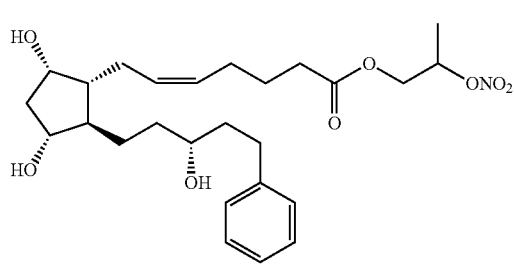
(82)
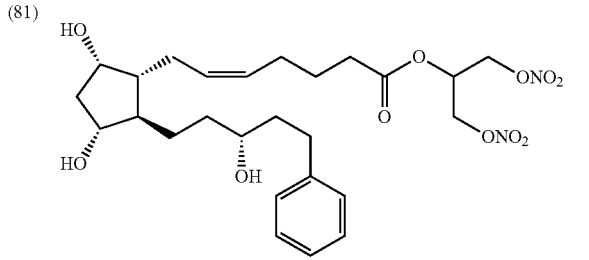
(83)
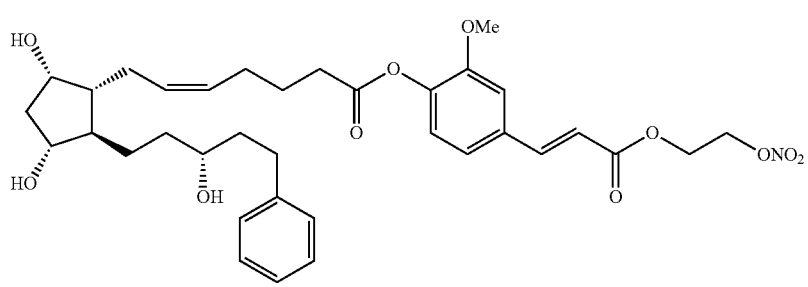
(84)
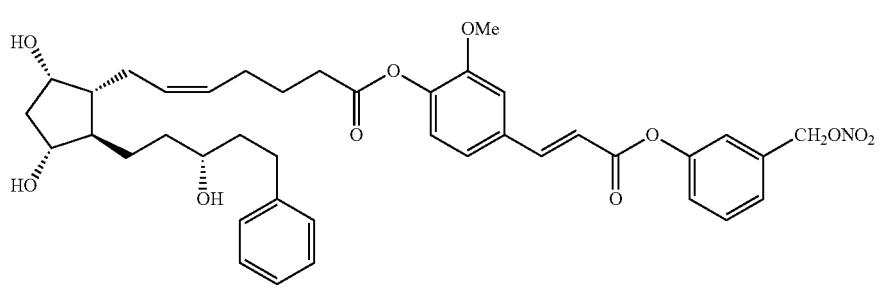

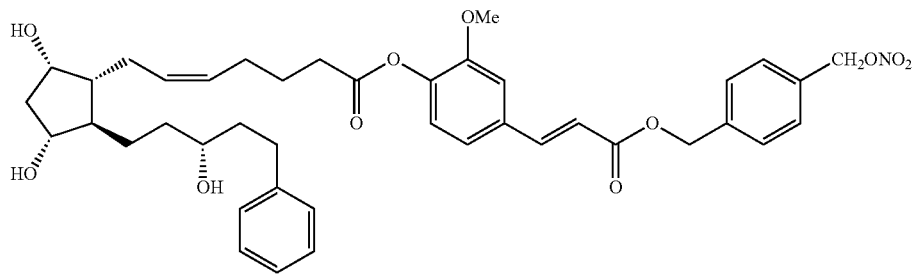
(85)
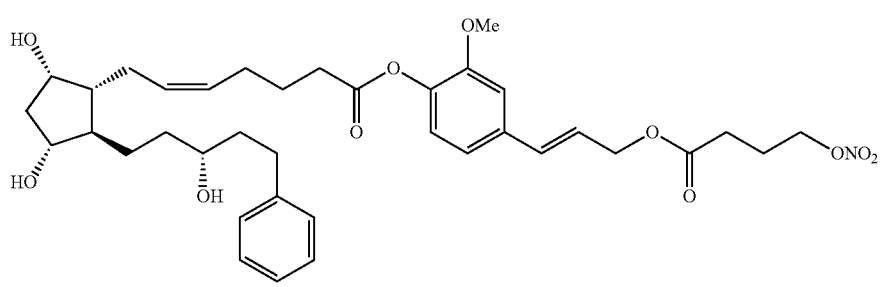
(86)
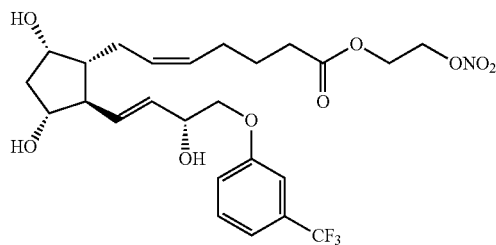
(87)
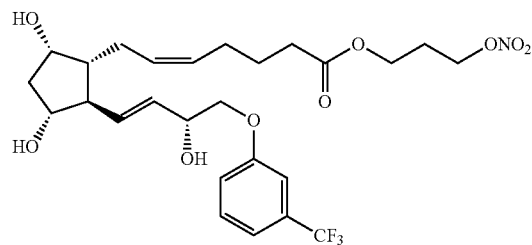
(88)
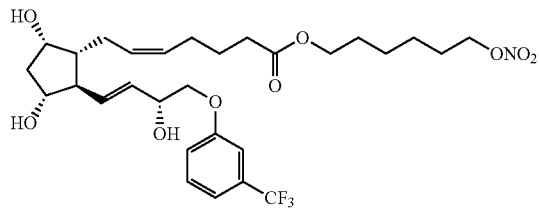
(89)
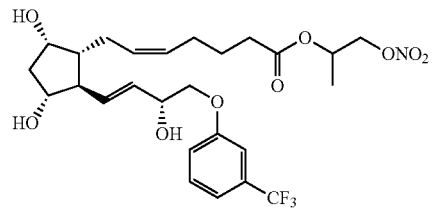
(90)
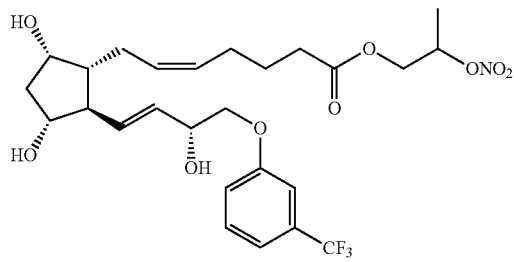
(91)
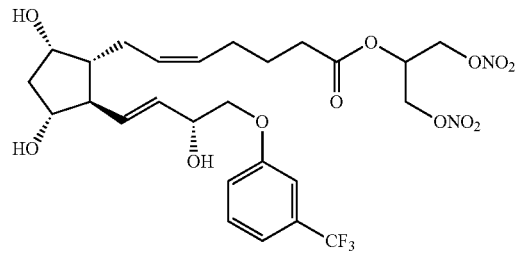
(92)

(93)
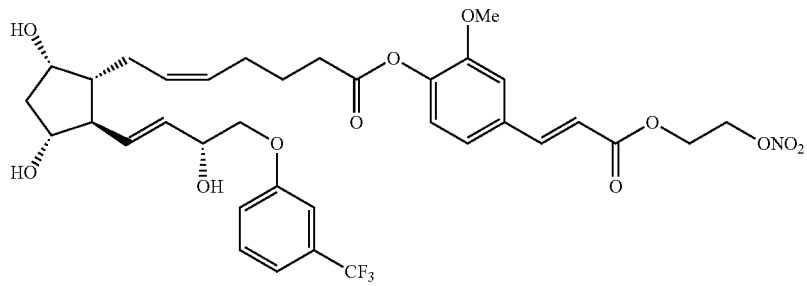
(94)
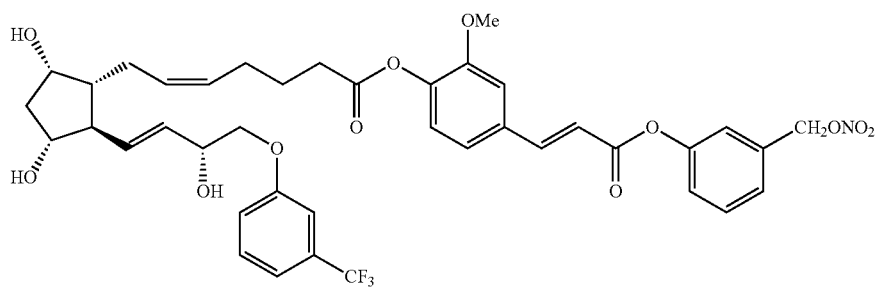
(95)
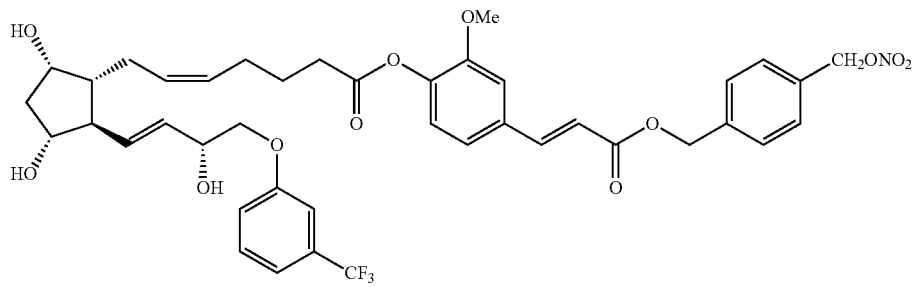
(96)
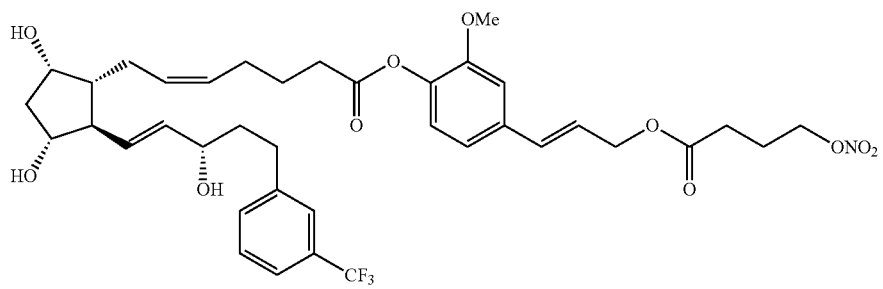
(97)
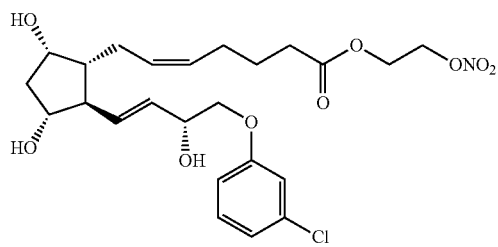
(98)
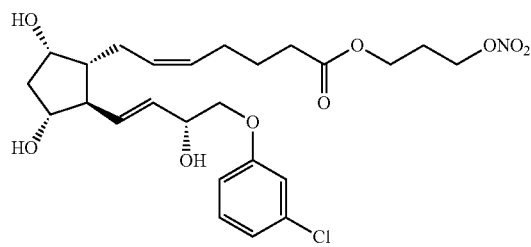

-continued
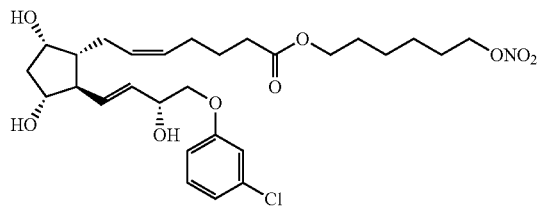 (99)
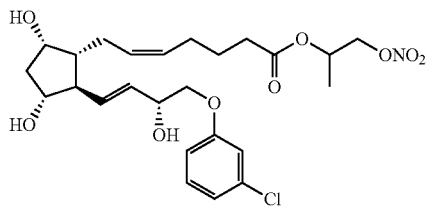 (100)
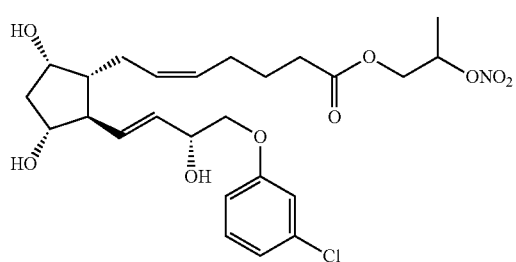 (101)
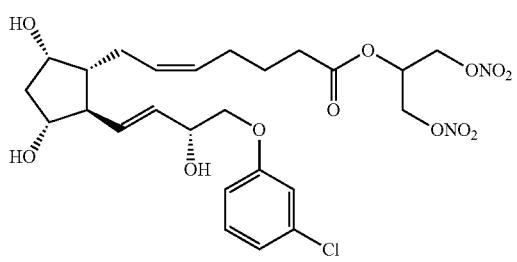 (102)
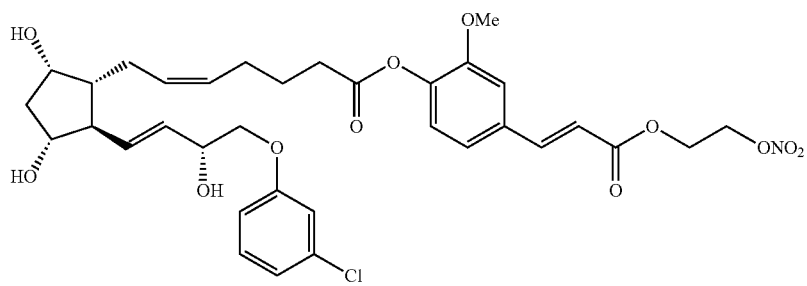 (103)
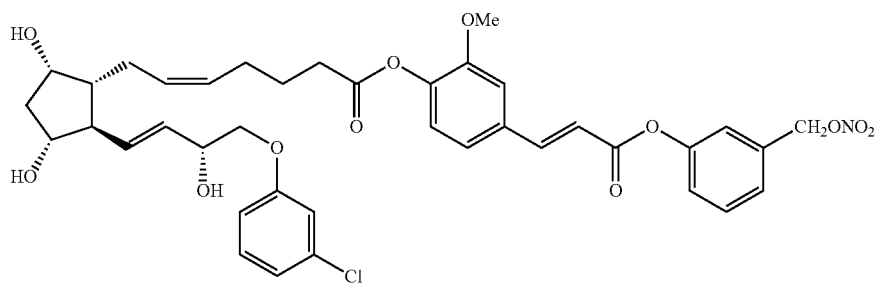 (104)
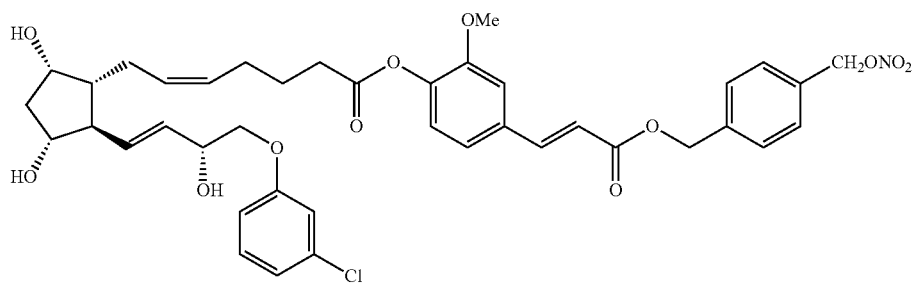 (105)
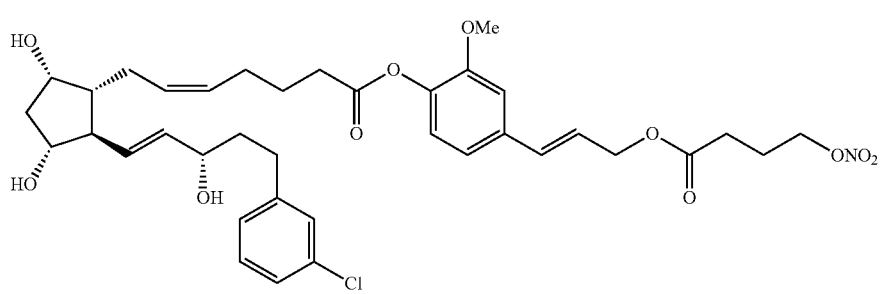 (106)

-continued
(107)
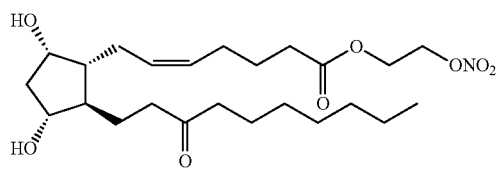
(108)
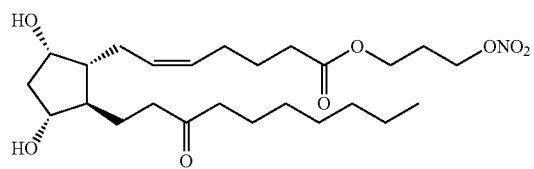
(109)
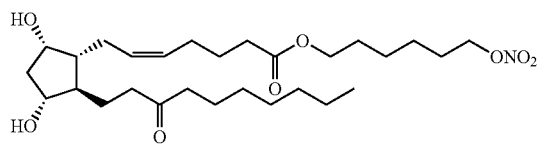
(110)
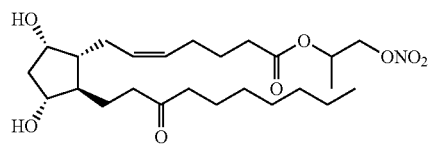
(111)
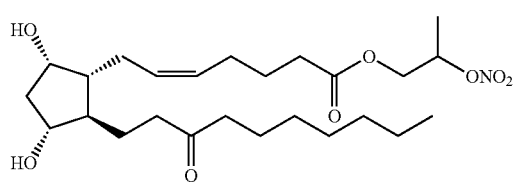
(112)
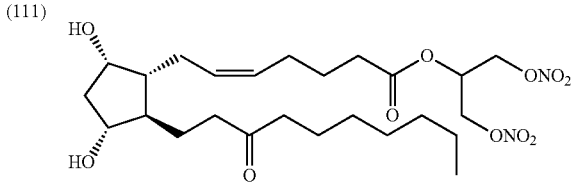
(113)
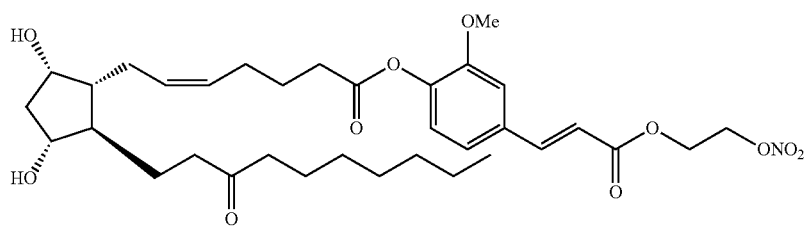
(114)
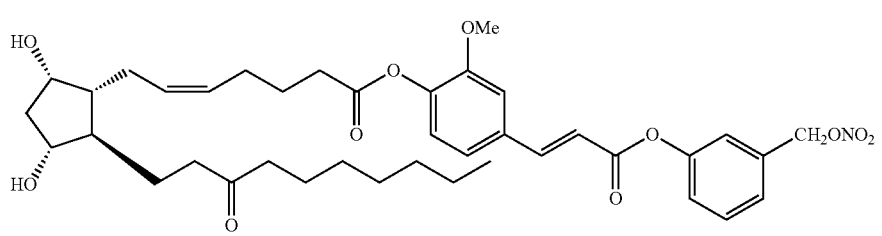
(115)
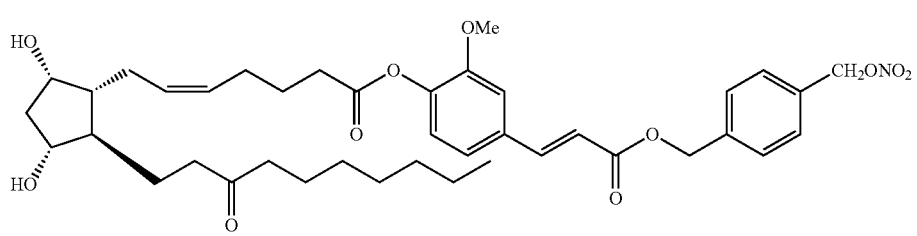
(116)
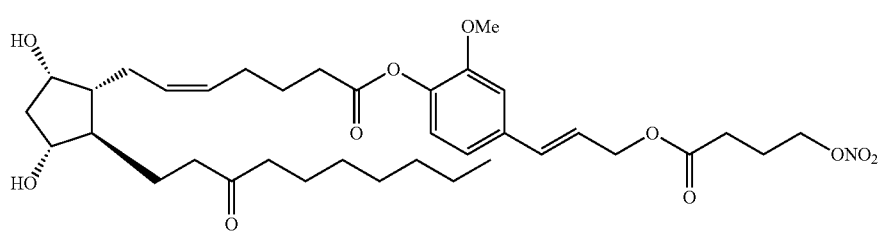

As mentioned above, objects of the present invention are also pharmaceutical compositions containing at least a compound of the present invention of formula (I) together with non toxic adjuvants and/or carriers usually employed in the pharmaceutical field.

The preferred route of administration is topical.

The compounds of the present invention can be administered as solutions, suspensions or emulsions (dispersions) in an ophthalmically acceptable vehicle. The term "ophthalmically acceptable vehicle" as used herein refers to any substance or combination of substances which are non-reactive with the compounds and suitable for administration to patient.

Preferred are aqueous vehicles suitable for topical application to the patient's eyes.

Other ingredients which may be desirable to use in the ophthalmic compositions of the present invention include antimicrobials, preservatives, co-solvents, surfactants and viscosity building agents.

The invention also relates to a method for treating glaucoma or ocular hypertension, said method consisting in contacting an effective intraocular pressure reducing amount of a composition with the eye in order to reduce eye pressure and to maintain said pressure on a reduced level.

The doses of prostaglandin nitroderivatives can be determined by standard clinical techniques and are in the same range or less than those described for the corresponding underivatized, commercially available prostaglandin compounds as reported in the: Physician's Desk Reference, Medical Economics Company, Inc., Oradell, N.J., 58$^{th}$ Ed., 2004; The pharmacological basis of therapeutics, Goodman and Gilman, J. G. Hardman, L. e. Limbird, Tenth Ed.

The compositions contain 0.1-0.30 µg, especially 1-10 µg, per application of the active compound.

The treatment may be advantageously carried out in that one drop of the composition, corresponding to about 30 µl, is administered about 1 to 2 times per day to the patient's eye.

It is further contemplated that the compounds of the present invention can be used with other medicaments known to be useful in the treatment of glaucoma or ocular hypertension, either separately or in combination. For example the compounds of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443. Also contemplated is the combination with nitrooxy derivatives of the above reported compounds, for example nitrooxy derivatives of beta-blockers such as those described in U.S. Pat. No. 6,242,432.

The compounds of the present invention can be synthesized as follows.

Synthesis Procedure

The compounds of general formula (I) as above defined, can be obtained:

i) by reacting a compound of formula (III)

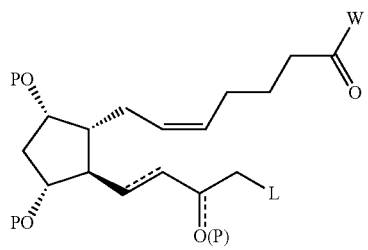

(III)

wherein

L is as above defined; P is H or a hydroxylic protecting group such as silyl ethers, such as trimethylsilyl, tert-butyl-dimethylsilyl or acetyl and those described in T. W. Greene "Protective groups in organic synthesis", Harvard University Press, 1980, 2$^{nd}$ edition, p. 14-118; W is —OH, Cl, or —OC(O)R$_1$ wherein R$_1$ is a linear or branched C$_1$-C$_5$ alkyl;

with a compound of formula (IV) Z—Y-Q wherein Y is as above defined, Z is HX or Z$_1$, being X as above defined and Z$_1$ selected from the group consisting of:

chlorine, bromine, iodine, mesyl, tosyl;

Q is —ONO$_2$ or Z$_1$ and ii) when Q is Z$_1$, by converting the compound obtained in the step i) into nitro derivative by reaction with a nitrate source such as silver nitrate, lithium nitrate, sodium nitrate, potassium nitrate, magnesium nitrate, calcium nitrate, iron nitrate, zinc nitrate or tetraalkylammonium nitrate (wherein alkyl is C$_1$-C$_{10}$ alkyl) in a suitable organic solvent such as acetonitrile, tetrahydrofurane, methyl ethyl ketone, ethyl acetate, DMF, the reaction is carried out, in the dark, at a temperature from room temperature to the boiling temperature of the solvent. Preferred nitrate source is silver nitrate and iii) optionally deprotecting the compounds obtained in step i) or ii) as described in T. W. Greene "Protective groups in organic synthesis", Harvard University Press, 1980, 2$^{nd}$ edition, p. 68-86. Fluoride ion is the preferred method for removing silyl ether protecting group.

The reaction of a compound of formula (III) wherein W=—OH, P and X$_1$ are as above defined, with a compound of formula (IV) wherein Y and Q are as above defined, Z is HX may be carried out in presence of a dehydrating agent as dicyclohexylcarbodiimide (DCC) or N'-(3-dimethylaminopropyl)-N-ethylcarbodiimide hydrochloride (EDAC) and a catalyst, such as N,N-dimethylamino pyridine (DMAP). The reaction is carried out in an inert organic solvent dry such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (III) wherein W=—OH and P=H are commercially available;

The compounds of formula (III) wherein W=—OH and P is a hydroxylic protecting group may be prepared from the corresponding compounds wherein P=H as well known in the art, for example as described in T. W. Greene "Protective groups in organic synthesis", Harvard University Press, 1980, 2$^{nd}$ edition, p. 14-118.

The reaction of a compound of formula (III) wherein W=—OC(O)R$_1$ wherein R$_1$ is as above defined and P=H or a hydroxylic protecting group, with a compound of formula (IV) wherein Y is as above defined, Z is —OH and Q is —ONO$_2$ may be carried out in presence of a catalyst, such as N,N-dimethylamino pyridine (DMAP). The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (III) wherein W=—OC(O)R$_1$ and P=H may be obtained from the corresponding acids wherein W=—OH by reaction with a chloroformate such as isobutylchloroformate, ethylchloroformate in presence of a non-nucleophilic base such as triethylamine in an inert organic solvent such as N,N'-dimethylformamide, tetrahydrofuran, a polyhalogenated aliphatic hydrocarbon at a temperature from −20° C. and 40° C. The reaction is completed within a time range from 1 to 8 hours.

The reaction of a compound of formula (III) wherein W=—OH and P=H, with a compound of formula (IV) wherein Y is as above defined, Z is Z$_1$ and Q is —ONO$_2$ may be carried out in presence of a organic base such as 1,8-diazabiciclo[5.4.0]undec-7-ene (DBU), N,N-diisopropylethylamine, diisopropylamine or inorganic base such as alkaline-earth metal carbonate or hydroxide, potassium carbonate, cesium carbonate, in an inert organic solvent such as N,N'-dimethylformamide, tetrahydrofuran, acetone, methyl ethyl ketone, acetonitrile, a polyhalogenated aliphatic hydrocarbon at a temperature from −20° C. and 40° C., preferably from 5° C. to 25° C. The reaction is completed within a time range from 1 to 8 hours. When Z$_1$ is chosen among chlorine or bromine the reaction is carried out in presence an iodine compound such as KI.

The reaction of a compound of formula (III) wherein W=Cl and P is as above defined, with a compound of formula (IV) wherein Y is as above defined, Z is —OH and Q is —ONO$_2$ may be carried out in presence of a of a organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (III) wherein W=Cl may be obtained from the corresponding acids wherein W=—OH by reaction with a thionyl or oxalyl chloride, halides of P$^{III}$ or P$^V$ in solvents inert such as toluene, chloroform, DMF.

The compounds of formula HO—Y—ONO$_2$, wherein Y is as above defined can be obtained as follows. The corresponding diol derivative, commercially available, or synthesized by well known reactions, is converted in HO—Y—Z$_1$, wherein Z$_1$ is as above defined, by well known reactions, for example by reaction with thionyl or oxalyl chloride, halides of P$^{III}$ or P$^V$, mesyl chloride, tosyl chloride in solvents inert such as toluene, chloroform, DMF, etc. The conversion to the nitro derivative is carried out as above described. Alternatively the diol derivative can be nitrated by reaction with nitric acid and acetic anhydride in a temperature range from −50° C. to 0° C. according to methods well known in the literature.

The compounds of formula Z$_1$—Y—ONO$_2$, wherein Y and Z$_1$ are as above defined can be obtained from the halogen derivative Z$_1$—Y-Hal, commercially available or synthesized according to methods well known in the literature, by conversion to the nitro derivative as above described.

The compounds of formula H—X—Y—Z$_1$, wherein X, Y and Z$_1$ are as above defined can be obtained from the hydroxyl derivative H—X—Y—OH, commercially available or synthesized according to methods well known in the literature, by well known reactions, for example by reaction with thionyl or oxalyl chloride, halides of P$^{III}$ or P$^V$, mesyl chloride, tosyl chloride in solvents inert such as toluene, chloroform, DMF, etc.

The following examples are to further illustrate the invention without limiting it.

Example 1

Synthesis of [1R-[1α(Z),2α(R*),3α,5α]]-7-[3,5-dihydroxy-2-(3-hydroxy-5-phenylpentyl)cyclopentyl]-5-heptenoic acid 4-(nitrooxy)butyl ester (compound 1)

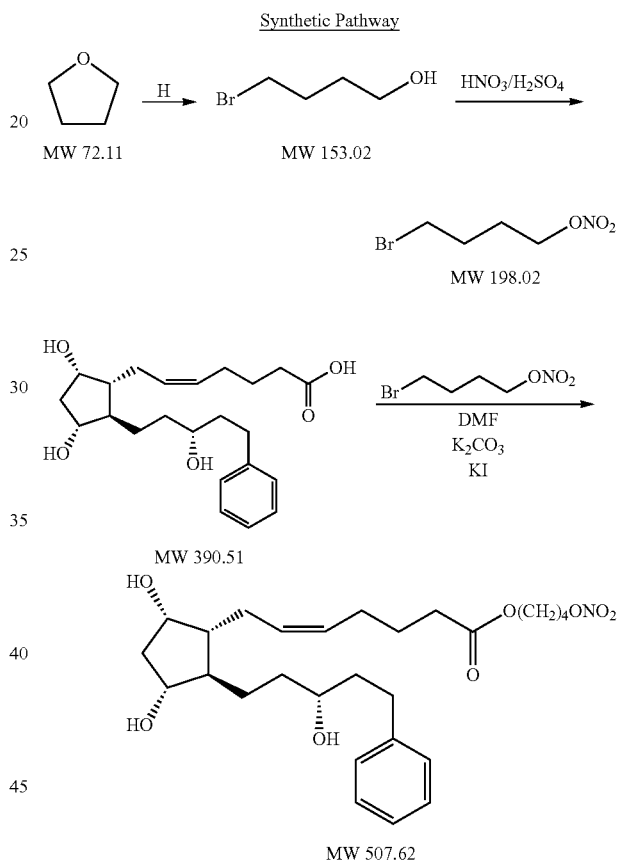

II Experimental

II.1 Preparation of 4-bromobutanol

Tetrahydrofuran (12.5 g-173 mmol) was charged under nitrogen in a reactor cooled to 5-10° C. Hydrogen bromide (7.0 g-86.5 mmol) was then added slowly and the reaction medium was stirred over a period of 4.5 hours at 5-10° C. The mixture was diluted with 22.5 g of cold water and the pH of this solution was adjusted to pH=5-7 by adding 27.65% sodium hydroxide (2.0 g) keeping the temperature at 5-10° C. The solution was then extracted twice with dichloromethane (13.25 g). The combined organic phases were washed with 25% brine (7.5 g), adjusted to pH=6-7 with 27.65% sodium hydroxide and dried over magnesium sulfate. Dichloromethane was distilled off and crude 4-bromobutanol (10.3 g-66.9 mmol) was obtained in a yield of about 77%.

II.2 Preparation of 4-bromobutyl nitrate

In reactor cooled to −5 to 5° C., nitric acid fuming (8.5 g-135 mmol) was slowly added to a solution of 98% sulfuric acid (13.0 g-130 mmol) in dichloromethane (18.0 g-212 mmol). 4-bromobutanol (10.2 g-66.6 mmol) was then added to this mixture and the reaction medium was stirred at −5 to 5° C. over a period of 2-5 hours. The mixture was poured into cold water (110 g) keeping the temperature between −5° C. and 3° C. After decantation, the upper aqueous phase was extracted with dichloromethane and the combined organic phases were washed with water, adjusted to pH=6-7 by addition of 27.65% sodium hydroxide, washed with brine and dried over magnesium sulfate. Dichloromethane was distilled off under vacuum and crude 4-bromobutyl nitrate (12.7 g-64.1 mmol) was recovered in a yield of about 96%.

II.3 Preparation of [1R-[1α(Z),2β(R*),3α,5α]]-7-[3,5-dihydroxy-2-(3-hydroxy-5-phenylpentyl)cyclopentyl]-5-heptenoic acid 4-(nitrooxy)butyl ester Latanoprost acid (97.7%, S-isomer <1%) (213 mg, 0.54 mmol) was dissolved in 5.0 g anhydrous DMF. $K_2CO_3$ (206 mg, 1.49 mmol), KI (77 mg, 0.46 mmol) and 4-bromobutylnitrate (805 mg, 25% w/w in methylene chloride, 1.02 mmol) were added. The reaction mixture was heated and stirred on a rotary evaporator at 45-50° C.

After 1.5 hour, TLC (Si, $CH_2Cl_2$-MeOH, 5%) showed no starting acid.

The reaction mixture was diluted with 100 ml ethyl acetate, washed with brine (3×50 ml), dried over $MgSO_4$ and evaporated to give yellowish oil (420 mg).

$^1$H NMR/$^{13}$C NMR showed target molecule as a major product together with some starting 4-bromobutylnitrate and DMF.

HPLC showed no starting acid. Residual solvent, 4-bromobutylnitrate and target ester were the main peaks. Butylnitrate ester showed similar UV spectrum as latanoprost and relative retention time was as expected.

Instrument: Bruker 300 MHz
Solvent: $CDCl_3$ $^1$H-NMR ($CDCl_3$) δ: 7.29-7.19 (5H, m, Ar); 5.45 (1H, m, CH=CH); 5.38 (1H, m, CH=CH); 4.48 (2H, t, $CH_2$—$ONO_2$); 4.18 (1H, m, CH—OH); 4.10 (2H, t, $COOCH_2$); 3.95 (1H, m, CH—OH); 3.68 (1H, m, CH—OH); 2.87-2.60 (2H, m); 2.35 (2H, t); 2.25 (2H, m); 2.13 (2H, m); 1.90-1.35 (16H, m).

$^{13}$C-NMR ($CDCl_3$) ppm: 173.94 (C=O); 142.14; 129.55 ($C_5$); 129.50 ($C_6$); 128.50; 125.93 78.80 ($C_{11}$); 74.50 ($C_9$); 72.70 (C—$ONO_2$); 71.39 ($C_{15}$); 63.57; 52:99 ($C_{12}$); 51.99 ($C_8$); 41.30 ($C_{10}$); 39.16 ($C_{16}$); 33.66; 32.21; 29.73; 27.04; 26.70; 25.04; 24.91; 23.72; 15.37.

Example 2

Synthesis of [1R-[1α(Z), 2β(R*),3α,5α]]-7-[3,5-dihydroxy-2-(3-hydroxy-5-phenylpentyl)cyclopentyl]-5-heptenoicacid[2-methoxy-4-[2-propenoyloxy (4-nitrooxybutyl)]]phenyl ester (compound 11)

A) Preparation of Ferulic acid 4-(bromo)butyl ester

To a solution of ferulic acid (1 g, 5.15 mmol) in tetrahydrofurane (40 ml), triphenylphosphine (2.7 g, 10.3 mmol) and tetrabromomethane (3.41 g, 10.3 mmol) were added. The mixture was stirred at room temperature for 4 hours. The mixture was filtered and the solvent was evaporated under vacuum. The crude residue was purified by silica gel chromatography, eluent n-hexane/ethyl acetate 7/3. The product (0.77 g) was obtained as a yellow solid. (Yield 46%)
M.p.=83-88° C.

B) Preparation of Ferulic acid 4-(nitrooxy)butyl ester

A solution of compound A (0.8 g, 2.43 mmol) and silver nitrate (1.2 g, 7.29 mmol) in acetonitrile (50 ml) was stirred at 40° C., in the dark, for 16 hours. The precipitate (silver salts) was filtered off and the solvent was evaporated under vacuum. The residue was purified by flash chromatography, eluent n-hexane/ethyl acetate 75/25. The product (0.4 g) was obtained as white powder (yield 53%)
M.p.=63-64° C.

C) Preparation of [1R-[1α(Z),2β(R*),3α,5α]]-7-[3,5-dihydroxy-2-(3-hydroxy-5-phenylpentyl)cyclopentyl]-5-heptenoic acid [2-methoxy-4-[2-propenoyloxy (4-nitrooxybutyl)]]phenyl ester To a solution of latanoprost acid (0.2 g, 0.15 mmol) in dry tetrahydrofuran (10 ml), in atmosphere inert, ferulic acid 4-(nitrooxy)butyl ester (0.32 g, 1.02 mmol) and DMAP (cat. amount) were added. The reaction was cooled at 0° C. and EDAC (0.14 g, 0.76 mmol) was added. The reaction was stirred at room temperature for 24 hours. The solution was treated with water and chloroform, the organic layers were anidrified with sodium sulfate and concentrated under reduced pressure. The residue was purified by flash chromatography, eluent n-hexane/ethyl acetate 3/7. The product (0.2 g) was obtained.

$^1$H-NMR ($CDCl_3$) δ: 7.55 (1H, d, CH=CHCO); 7.30-7.03 (8H, m, Ar); 6.35 (1H, d, CH=CHCO); 5.48 (2H, m, CH=CH); 4.52 (2H, t, $CH_2$—$ONO_2$); 4.25 (2H, t, COO—$CH_2$); 4.17 (1H, m, CH—OH); 3.95 (1H, m, CH—OH); 3.85 (3H, s, $OCH_3$); 3.65 (1H, m, CH—OH); 2.75 (2H, m); 2.61 (2H, t); 2.48-2.20 (5H, m); 1.9-1.20 (19H, m).

$^{13}$C-NMR ($CDCl_3$): ppm: 171.62 (C=O); 166.69 (C=O); 151.40; 144.36; 142.04; 141.55; 133.21; 129.62; 129.41; 128.40; 125.85, 123.27; 121.27; 117.96; 111.32; 78.81; 74.84; 72.64 (C—$ONO_2$); 71.32; 63.61; 55.94; 52.99; 51.91; 42.54; 39.08; 35.79; 33.37; 32.12; 29.68; 27.03; 26.53; 25.09; 24.90; 23.73.

Example 3

Synthesis of [1R-[1α(Z),2β(R*),3α,5α]]-7-[3,5-dihydroxy-2-(3-hydroxy-5-phenylpentyl)cyclopentyl]-5-heptenoic acid 3-(nitrooxymethyl)phenyl ester (compound 4)

1. Preparation of 3-[(Bromo)methyl]phenol

3-[(Hydroxy)methyl]phenol was dissolved in acetonitrile (300 ml) and dichloromethane (900 ml) and the resulting mixture was poured in the flask kept under argon; magnetic stirring was set on. The solution was then cooled with an ice bath and carbon tetrabromide and triphenilphosphine were added. The latter was added in small portions in order to maintain the temperature at ca. 2-3° C.

The solution was stirred for 1 hour at 2-3° C. and then for an additional hour at room temperature.

After this period the reaction conversion (checked by TLC, using EtOAc/Petroleum ether 3/7 as the eluent) was complete. The obtained mixture was evaporated under reduce pressure and 500 ml of petroleum ether and 500 ml of EtOAc were added to the resulting yellow thick oil in a 2 l round flask. A pitchy solid was formed. The mixture was kept under stirring at room temperature overnight and subsequently filtered and concentrated under reduce pressure, furnishing ca. 50 g of an oily residue. The oil was purified by flash chromatography over 600 g of silica gel, using EtOAc/Petroleum ether 2/8 as the eluent. Further purification was achieved by crystallising the resulting bromide from petroleum ether.

A white solid was obtained (24 g, 64%).

Analysis

TLC: (EtOAc/Petroleum ether 3/7) Rf=0.4

HPLC purity: >98%

FT-IR (KBr, cm$^{-1}$): 3252, 1589, 1479, 1392, 1270, 1208, 1155, 952, 880, 791, 741, 686.

2. Preparation of 3-[(Nitrooxy)methyl]phenol

3-[(Bromo)methyl]phenol was dissolved in 30 ml of acetonitrile and poured in the flask, kept far from light sources at 0-5° C. under argon; magnetic stirring was set on. Silver nitrate was then added under these conditions, maintaining the temperature under 5° C. The reaction course was followed by TLC (EtOAc/Petroleum ether 3/7 as the eluent). After 4 hours and 30 minutes the conversion was complete. The reaction mixture was then filtered, the precipitated solid was washed with Et$_2$O and the filtrate was separated in two batches. The first batch (15 ml) was kept under argon and in acetonitrile solution at −20° C. The second batch (15 ml) was worked-up as follows. The acetonitrile solution was concentrated under reduce pressure and the resulting oil was dissolved in dichloromethane (15 ml) and washed with brine (15 ml). The organic phase was separated and the aqueous phase was extracted twice with dichloromethane (2×25 ml). The combined organic phases were then dried over MgSO$_4$, filtered and evaporated. The residue was purified by flash chromatography over 40 g of silica gel using EtOAc/Petroleum ether 2/8 as the eluent. The nitrate was obtained as an oil (0.6 g, 67%).

Analysis

TLC: (EtOAc/Petroleum ether 3/7) Rf=0.35

HPLC purity: >98%

MS (ESI−): 168 (M$^+$−1)

FT-IR (neat oil, cm$^{-1}$): 3365, 1632, 1599, 1459, 1282, 1160, 923, 867, 793, 757.

$^1$H NMR (CDCl$_3$, 300 MHz) δ 5.31 (2H, s), 5.45 (1H, br s), 6.78-6.84 (2H, m), 6.87-6.92 (1H, m), 7.17-7.24 (1H, m).

3. Preparation of [1R-[1α(Z),2α(R*),3α,5α]]-7-[3,5-dihydroxy-2-(3-hydroxy-5-phenylpentyl)cyclopentyl]-5-heptenoic acid 3-(nitrooxymethyl)phenyl ester To a solution of latanoprost acid (0.11 g, 0.28 mmol) in chloroform (20 ml), in atmosphere inert, 3-(nitrooxymethyl)phenol (0.01 g, 0.56 mmol) and DMAP (cat. amount) were added. The reaction was cooled at 0° C. and EDAC (0.08 g, 0.42 mmol) was added. The reaction was stirred at room temperature for 24 hours. The solution was treated with water, the organic layers were anidrified with sodium sulfate and concentrated under reduced pressure. The residue was purified by flash chromatography, eluent n-hexane/ethyl acetate 3/7. The product (0.1 g) was obtained.

$^1$H-NMR (CDCl$_3$) δ: 7.41 (1H, t, Ar); 7.31-7.10 (8H, m, Ar); 5.48 (2H, m, CH=CH); 5.43 (2H, s, CH$_2$—ONO$_2$); 4.16 (1H, m, CH—OH); 3.95 (1H, m, CH—OH); 3.65 (1H, m, C H—OH); 2.75 (2H, m); 2.61 (2H, t); 2.48-2.20 (5H, m); 1.9-1.20 (11H, m).

Example 4

Synthesis of [1R-[1α(Z),2β(R*),3α,5α]]-7-[3,5-dihydroxy-2-(3-hydroxy-5-phenylpentyl)cyclopentyl]-5-heptenoic acid 4-(nitrooxymethyl)benzyl ester (compound 9)

A) [1R-[1α(Z),2β(R*),3α,5α]]-7-[3,5-dihydroxy-2-(3-hydroxy-5-phenylpentyl)cyclopentyl]-5-heptenoic acid 4-(bromomethyl)benzyl ester To a solution of latanoprost acid (0.5 g, 1.2 mmol) in chloroform (50 ml), in inert atmosphere, 4-(bromomethyl)benzyl alcohol (0.4 g, 1.92 mmol) and DMAP (cat. amount) were added. The reaction was cooled at 0° C. and EDAC (0.37 g, 1.92 mmol) was added. The reaction was stirred at room temperature for 5 hours. The solution was treated with water, the organic layers were anidrified with sodium sulfate and concentrated under reduced pressure. The residue was purified by flash chromatography, eluent n-hexane/ethyl acetate 3/7. The product (0.47 g) was obtained.

B) [1R-[1α(Z),2β(R*),3α,5α]]-7-[3,5-dihydroxy-2-(3-hydroxy-5-phenylpentyl)cyclopentyl]-5-heptenoic acid 4-(nitrooxymethyl)benzyl ester A solution of compound A (0.4 g, 0.7 mmol) and silver nitrate (0.23 g, 1.4 mmol) in acetonitrile (50 ml) was stirred at 40° C., in the dark, for 4 hours. The precipitated (silver salts) was filtered off and the solvent was evaporated under vacuum. The residue was purified by flash chromatography, eluent n-hexane/ethyl acetate 7/3. The product (0.15 g) was obtained as oil.

$^1$H-NMR δ: 7.39 (4H, s, Ar); 7.31-7.17 (5H, m, Ar); 5.44 (2H, m, CH=CH); 5.42 (2H, s, CH$_2$—ONO$_2$); 5.30 (2H, s, O—CH$_2$—Ar); 4.15 (1H, m, CH—OH); 3.95 (1H, m, CH—OH); 3.67 (1H, m, CH—OH); 2.75 (2H, m); 2.41 (2H, t); 2.48-1.20 (16H, m).

Example 5

Synthesis of [1R-[1α(Z),2β(R*),3α,5α]]-7-[3,5-dihydroxy-2-(3-hydroxy-5-phenylpentyl)cyclopentyl]-5-heptenoic acid 3-(nitrooxy)propyl ester (compound 78)

The compound is synthesized using the procedure described in EXAMPLE 4 starting from latanoprost acid and 3-bromopropanol.

Example 6

Synthesis of [1R-[1α(Z),2β(R*),3α,5α]]-7-[3,5-dihydroxy-2-(3-hydroxy-5-phenylpentyl)cyclopentyl]-5-heptenoic acid 2-(nitrooxy)ethyl ester (compound 77)

The compound is synthesized using the procedure described in EXAMPLE 4 starting from latanoprost acid and 2-bromoethanol.

Example 7

Synthesis of [1R-[1α(Z),2β(R*),3α,5α]]-7-[3,5-dihydroxy-2-(3-hydroxy-5-phenylpentyl)cyclopentyl]-5-heptenoic acid 6-(nitrooxy)hexyl ester (compound 79)

The compound is synthesized using the procedure described in EXAMPLE 4 starting from latanoprost acid and 6-bromohexanol.

Example 8

Synthesis of [1R-[1α(Z),2β(R*),3α,5α]]-7-[3,5-dihydroxy-2-(3-hydroxy-5-phenylpentyl)cyclopentyl]-5-heptenoic acid 2-(nitrooxy)-1-methylethyl ester (compound 80)

The compound is synthesized using the procedure described in EXAMPLE 4 starting from latanoprost acid and 1-bromo-2-propanol.

Example 9

Synthesis of [1R-[1α(Z),2β(R*),3α,5α]]-7-[3,5-dihydroxy-2-(3-hydroxy-5-phenylpentyl)cyclopentyl]-5-heptenoic acid 2-(nitrooxy)propyl ester (compound 81)

The compound is synthesized using the procedure described in EXAMPLE 4 starting from latanoprost acid and 2-chloro-1-propanol.

Example 10

Synthesis of [1R-[1α(Z),2β(R*),3α,5α]]-7-[3,5-dihydroxy-2-(3-hydroxy-5-phenylpentyl)cyclopentyl]-5-heptenoic acid 2-(nitrooxy)-1-(nitrooxymethyl)ethyl ester (compound 82)

The compound is synthesized using the procedure described in EXAMPLE 4 starting from latanoprost acid and 1,3-dibromo-2-propanol.

Example 11

Synthesis of [1R-[1α(Z),2β(R*),3α,5α]]-7-[3,5-dihydroxy-2-(3-hydroxy-5-phenylpentyl) cyclopentyl]-5-heptenoic acid [2-methoxy-4-[2-propenoyloxy (2-nitrooxyethyl)]]phenyl ester (compound 83)

The compound is synthesized using the procedure described in EXAMPLE 2 starting from latanoprost acid and ferulic acid 2-(nitrooxy)ethyl ester.

Example 12

Synthesis of [1R-[1α(Z),2β(R*),3α,5α]]-7-[3,5-dihydroxy-2-(3-hydroxy-5-phenylpentyl)cyclopentyl]-5-heptenoic acid 2-methoxy-4-[2-propenoyloxy (3-nitrooxmethylphenyl)]]phenyl ester (compound 84)

The compound is synthesized using the procedure described in EXAMPLE 2 starting from latanoprost acid and ferulic acid 3-(nitrooxymethyl)phenyl ester.

Example 13

Synthesis of [1R-[1α(Z),2β(R*),3α,5α]]-7-[3,5-dihydroxy-2-(3-hydroxy-5-phenylpentyl)cyclopentyl]-5-heptenoic acid 2-methoxy-4-[2-propenoyloxy (4-nitrooxmethylbenzyl)]]phenyl ester (compound 85)

The compound is synthesized using the procedure described in EXAMPLE 2 starting from latanoprost acid and ferulic acid 4-(nitrooxymethyl)benzyl ester.

Example 14

Synthesis of [1R-[1α(Z),2β(R*),3α,5α]]-7-[3,5-dihydroxy-2-(3-hydroxy-5-phenylpentyl)cyclopentyl]-5-heptenoic acid (4-nitrooxmethyl)phenyl ester (compound 6)

The compound is synthesized using the procedure described in EXAMPLE 4 starting from latanoprost acid 4-(chloromethyl)phenyl ester.

Example 15

Synthesis of [1R-[1α(Z),2β(R*),3α,5α]]-7-[3,5-dihydroxy-2-(3-hydroxy-5-phenylpentyl)cyclopentyl]-5-heptenoic acid (3-nitrooxmethyl)benzyl ester (compound 8)

The compound is synthesized using the procedure described in EXAMPLE 4 starting from latanoprost acid 4-(bromomethyl)benzyl ester.

Example 16

Preparation of an ophthalmic composition using [1R-[1α(Z),2α(R*),3α,5α]]-7-[3,5-dihydroxy-2-(3-hydroxy-5-phenylpentyl)cyclopentyl]-5-heptenoic acid 4-(nitrooxy)butyl ester (compound 1)

| Ingredient | Amount (mg/ml) |
|---|---|
| Compound 1 | 0.1 |
| Tween 80 | 5 |
| Benzalkonium chloride | 0.2 |
| Buffer | q.s. |

Buffer:
NaCl   4.1 mg/ml
NaH$_2$PO$_4$ (anh.)   4.74 mg/ml
NaH$_2$PO$_4$ (monohyd.)   4.6 mg/ml
water for injection   qs.

Example 17

Evaluation of Nitric Oxide-Mediated Activity

The formation of cyclic guanosine-3',5' monophosphate (cGMP) in cells in the eye is involved in the regulation of aqueous humor flow. Thus, elevation of cGMP levels leads to decreased aqueous humor production and reduction of intraocular pressure.

We measured the effects of test drugs on cGMP formation in a well established cell assay.

Undifferentiated pheochromocytoma cells (PC12) were used. The monolayer cells were incubated for 45 min in Hank's Balanced Salt Solution enriched with 10 mM Hepes, 5 mM $MgCl_2$ and 0.05% ascorbic acid at the final pH of 7.4 and containing 100 µM of the phosphodiesterase inhibitor, isomethyl-butyl-xanthine (IBMX), 30 µM of the guanylyl cyclase inhibitor, YC-1, and the test drugs at the appropriate concentration. The reaction was terminated by the removal of the incubating buffer followed by the addition of 50 L of 100% ice-cold ethanol. The plate was then dried under hot air steam and the residue dissolved, extracted and analysed using commercially available cyclic cGMP enzyme immunoassay kit.

The results are reported in Table 1. The concomitant application of different concentrations of the various Latanoprost nitroderivatives (1-50 µM) elicited cGMP accumulation in a concentration-dependent fashion.

These effects were not shared by the parent drug Latanoprost suggesting that such effects are dependent on the release of exogenous NO.

TABLE 1

Potency and Efficacy of Latanoprost and respective nitroderivatives on cGMP accumulation in rat pheochromocytoma cells.

| Drugs | $EC_{50}$ (µM) | $E_{max}$ (% over vehicle) |
|---|---|---|
| Latanoprost | Not effective | Not effective |
| Compound 1 (ex. 1) | 2.4 | 290 |
| Compound 4 (ex. 3) | 4.4 | 450 |
| Compound 11 (ex. 2) | 1.5 | 480 |

$EC_{50}$ = effective concentration producing half maximal response
$E_{max}$ = maximum effect Example 18

Evaluation of the Efficacy of Latanoprost Nitroderivative on Intraocular Pressure Male NZW rabbits ranging from 3-5 kgs of body weight were used in this study. Briefly, the ability of Latanoprost nitroderivative (compound 4, EXAMPLE 3) at reducing intraocular pressure (IOP) was tested in animals previously treated with intracameral injection of 0.25% carbomer solution installation until after a stable increase of the intraocular pressure was reached. In this particular study, test drugs were administered to one eye with the dosage schedule of 1 drop/eye/day for 5 days a week with a physiologic solution containing 0.005% of control or test compounds. The IOP was monitored 3 h after drug application, two-three times weekly for a total of 4 weeks. This concentration was chosen as it reflects that of latanoprost isopropyl ester currently used in clinic to treat the increase of IOP observed in glaucoma patients. Furthermore, at each visit, about 200 µl of aqueous humor was collected using a 30 gauge needle from both eyes under lidocaine anesthesia for further biochemical evaluation of cGMP, camp and nitrite/nitrate contents.

The installation of 0.25% carbomer solution into the eye resulted in a profound increase of the IOP to about 40 mmHg that remained stable thereafter. However, the administration of the compound 4 (EX. 3) with the dose schedule outline in the method session, decreased the intraocular pressure of these animals of about 50% within 7 days of repeated treatments and over 65% by the end of the study (See Table 2). In contrast, neither Latanoprost acid (data not shown) nor its isopropyl derivative elicited any appreciable change (see Table 2). Given the literature available documenting that Latanoprost is virtually not effective in rabbits, the observed effects are likely to be attributed to the presence of the nitric oxide (NO) moiety onto Latanoprost nitroderivative rather than the parent compound.

Biochemical measurements of cGMP, cAMP and NOx in the intraocular aqueous humor further supported the role of NO at decreasing the IOP of these animals. In fact, as shown in Table 3, the extent of cGMP and NOx increased following the application of the compound 4 (EX. 3) over the 4-week treatment. These effects turn out to be highly specific as the amount of intraocular cAMP remained unaltered in these animals. Latanoprost isopropyl ester did not significantly affect the levels of either cGMP, cAMP or nitrites when given at equimolar doses to that of the respective nitroderivative (see Table 3).

TABLE 2

Reversal of stimuli carbomer-evoked increase in IOP before (pre-treatment) and after eye-installation of equimolar Latanoprost isopropyl ester or the respective nitroderivative

| IOP mmHg | Pre-treatment* | Day 2 | Day 7 | Day 10 | Day 15 | Day 17 | Day 23 | Day 25 |
|---|---|---|---|---|---|---|---|---|
| Latanoprost isopropyl ester | 37 ± 2 | 34 ± 2 | 33 ± 3 | 30 ± 1 | 31 ± 2 | 30 ± 2 | 32 ± 2 | 30 ± 2 |
| Compound 4 (ex. 3) | 42 ± 2 | 31 ± 1 | 26 ± 1 | 20 ± 1 | 18 ± 2 | 16 ± 1 | 15 ± 1 | 14 ± 1 |

*Pre-treatment values correspond to baseline IOP evoked following the intracameral installation of 0.25% carbomer solution.

TABLE 3

Effects of Latanoprost isopropyl ester and the respective nitroderivative on cGMP, cAMP and NOx content in carbomer-treated rabbits.

| IOP mmHg | Pre-treatment* | I Week | II Week | III Week | IV Week |
|---|---|---|---|---|---|
| cGMP (fmol/mg prot) | | | | | |
| Latanoprost isopropyl ester | 87 ± 6 | 88 ± 6 | 98 ± 6 | 99 ± 6 | 100 ± 6 |
| Compound 4 (ex. 3) | 88 ± 5 | 102 ± 5 | 125 ± 5 | 140 ± 5 | 160 ± 5 |
| cAMP (fmol/mg prot) | | | | | |
| Latanoprost isopropyl ester | 510 ± 18 | 550 ± 22 | 600 ± 30 | 620 ± 31 | 625 ± 31 |
| Compound 4 (ex. 3) | 520 ± 20 | 600 ± 25 | 650 ± 31 | 680 ± 28 | 660 ± 22 |
| NOx (nmol/mg prot) | | | | | |
| Latanoprost isopropyl ester | 16 ± 1 | 18 ± 2 | 18 ± 1 | 19 ± 2 | 19 ± 2 |
| Compound 4 (ex. 3) | 17 ± 1 | 22 ± 2 | 25 ± 3 | 26 ± 3 | 28 ± 3 |

*Pre-treatment values correspond to baseline IOP evoked following the intracameral installation of 0.25% carbomer solution.

The invention claimed is:

1. A compound of formula (I):

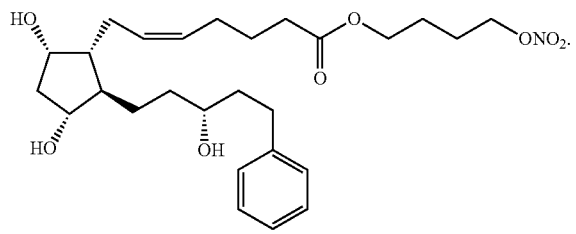

(I)

2. A method for treating or controlling glaucoma or ocular hypertension, said method comprising contacting an effective intraocular pressure reducing amount of a compound of formula (I) according to claim 1 with the eye of a subject in order to reduce eye pressure and to maintain said pressure on a reduced level.

* * * * *